(12) United States Patent
Annunziata et al.

(10) Patent No.: US 10,533,208 B2
(45) Date of Patent: *Jan. 14, 2020

(54) METHODS OF TREATING DEMENTIA ASSOCIATED WITH ALZHEIMER'S DISEASE WITH PROTECTIVE PROTEIN/CATHEPSIN A (PPCA)

(71) Applicant: St. Jude Children's Research Hospital, Memphis, TN (US)

(72) Inventors: Ida Annunziata, Memphis, TN (US); Alessandra D'Azzo, Memphis, TN (US)

(73) Assignee: ST. JUDE CHILDREN'S RESEARCH HOSPITAL, Memphis, TN (US)

(*) Notice: Subject to any disclaimer, the term of this patent is extended or adjusted under 35 U.S.C. 154(b) by 6 days.

This patent is subject to a terminal disclaimer.

(21) Appl. No.: 15/808,075

(22) Filed: Nov. 9, 2017

(65) Prior Publication Data

US 2018/0057854 A1 Mar. 1, 2018

Related U.S. Application Data

(63) Continuation of application No. 15/187,349, filed on Jun. 20, 2016, now Pat. No. 9,840,727, which is a continuation of application No. 14/239,728, filed as application No. PCT/US2012/052629 on Aug. 28, 2012, now Pat. No. 9,399,791.

(60) Provisional application No. 61/544,855, filed on Oct. 7, 2011, provisional application No. 61/529,675, filed on Aug. 31, 2011.

(51) Int. Cl.
| | |
|---|---|
| *A61K 38/47* | (2006.01) |
| *C12Q 1/34* | (2006.01) |
| *G01N 33/574* | (2006.01) |
| *A61K 38/48* | (2006.01) |
| *G06F 19/00* | (2018.01) |
| *G01N 33/573* | (2006.01) |

(52) U.S. Cl.
CPC ............ *C12Q 1/34* (2013.01); *A61K 38/47* (2013.01); *A61K 38/48* (2013.01); *A61K 38/4813* (2013.01); *C12Y 302/01018* (2013.01); *G01N 33/573* (2013.01); *G01N 33/57484* (2013.01); *G01N 33/57496* (2013.01); *G06F 19/34* (2013.01); *G01N 2333/924* (2013.01); *G01N 2800/2821* (2013.01); *G01N 2800/56* (2013.01)

(58) Field of Classification Search
CPC ............ C12Q 1/34; G01N 2800/2821; G01N 33/57484; G01N 2333/924; A61K 38/47; A61K 38/48; G06F 19/34
USPC ........................................ 424/94.61; 435/18
See application file for complete search history.

(56) References Cited

U.S. PATENT DOCUMENTS

| | | | |
|---|---|---|---|
| 7,232,670 | B2 | 6/2007 | D'Azzo et al. |
| 7,241,442 | B2 | 7/2007 | D'Azzo et al. |
| 7,273,716 | B2 | 9/2007 | McDermott |
| 7,951,367 | B2 | 5/2011 | Gan et al. |
| 8,388,953 | B2 | 3/2013 | Gan et al. |
| 8,420,613 | B2 | 4/2013 | Gan et al. |
| 8,691,519 | B2 | 4/2014 | Gan et al. |
| 8,796,236 | B2 | 8/2014 | Dodge et al. |
| 2002/0006959 | A1 | 1/2002 | Henderson |
| 2011/0166074 | A1 | 7/2011 | Maxfield et al. |
| 2014/0161896 | A1 | 6/2014 | Peer et al. |
| 2014/0234302 | A1 | 8/2014 | Gan et al. |

FOREIGN PATENT DOCUMENTS

| | | |
|---|---|---|
| WO | WO 97/15588 A1 | 5/1997 |
| WO | WO 98/31817 | 7/1998 |
| WO | WO 2006/013013 A2 | 2/2006 |
| WO | WO 2011/049787 A1 | 4/2011 |

OTHER PUBLICATIONS

Annunziata, I., et al, "Lysosomal NAEU1 defiiency affects amyloid precursor protein levels and amyloid-B secretion via deregulatesd lysosomal exocytosis," *Nature Communications*, 2013, vol. 4, pp. 1-12.

Bonten et al., "Targeting macrophages with baculovirus-produced lysosomal enzymes: implications for enzyme replacement therapy of theglycoprotein storage disorder galactosialidosis," *The FASEB Journal*, 2004, vol. 18(9), pp. 1-21.

(Continued)

*Primary Examiner* — Julie Wu
*Assistant Examiner* — Paul C Martin
(74) *Attorney, Agent, or Firm* — Womble Bond Dickinson (US) LLP

(57) ABSTRACT

Methods are provided for the prognosis, diagnosis and treatment of various pathological states, including cancer, chemotherapy resistance and dementia associated with Alzheimer's disease. The methods provided herein are based on the discovery that various proteins with a high level of sialylation are shown herein to be associated with disease states, such as, cancer, chemotherapy resistance and dementia associated with Alzheimer's disease. Such methods provide a lysosomal exocytosis activity profile comprising one or more values representing lysosomal exocytosis activity. Also provided herein, is the discovery that low lysosomal sialidase activity is associated with various pathological states. Thus, the methods also provide a lysosomal sialidase activity profile, comprising one or more values representing lysosomal sialidase activity. A lysosomal sialidase activity profile is one example of a lysosomal exocytosis activity profile.

16 Claims, 2 Drawing Sheets
Specification includes a Sequence Listing.

(56) References Cited

OTHER PUBLICATIONS

Budiu, R. A., et al., "Soluble MUC1 and serum MUC1-specific antibodies are potential prognostic biomarkers for platinum-resistant ovarian cancer," *Cancer Immunol. Immunother.*, 2011, vol. 60, pp. 975-984.

Breitner, John C.S., "The Role of Anti-Inflammatory Drugs in the Prevention and Treatment of Alzheimer's Disease," *Annu. Rev. Med.*, 1996, vol. 47, pp. 401-411.

D'Azzo and Bonten, "Molecular Mechanisms of Pathogenesis in a Glycosphigolipid and a Glycoprotein Storage Disease," *Biochem. Soc. Trans.* 38(6):1453-1457 (2010).

Doraiswamy, P., et al., "Pharmacological strategies for the prevention of Alzheimer's disease," *Expert Opin. Pharmacother.*, 2006,vol. 7(1), pp. 1-10.

Eimer and Vassar, "Neuron loss in the 5XFAD mouse model of Alzheimer's disease correlates with intraneuronal A$\beta_{42}$ accumulation and Caspase-3 activation," Molecular Neurodegeneration 8:2 (2013).

Fehrenbacher, N., et al., "Sensitization to the Lysosomal Cell Death Pathway by Oncogene-Induced Down-regulation of Lysosome-Associated Membrane Proteins 1 and 2," *Cancer Res.*, 2008, vol. 68, No. 16, pp. 6623-6633.

Gan, "Amyloid β Degradation & Inflammation: New Therapeutic Strategies in AD," ADC Directors' Meeting, Chicago, Apr. 12, 2008, retrieved from: www.alz.washington.edu/NONMEMBER/SPR08/gan.pdf, 77 pages.

Hahn et al., "Correction of murine galactosialidosis by bone marrow-derived macrophages overexpressing human protective protein/cathepsin A under control of the colony-stimulating factor-1 receptor promoter," *Proc. Natl. Acad. Sci. USA* 95(25):14880-14885 (1998).

Leimig, T., et al., "Functional amelioration of murine galactosialidosis by genetically modified bone marrow hematopoietic progenitor cells," *Blood*, 2002, vol. 99(9), pp. 3169-3178.

Lison et al., "Disrupted cross-laminar cortical processing in b amyloid pathology precedes cell death," *Neurobiology of Disease* 63:62-73 (2014).

MacDonald et al., "Cerebral Glucose Metabolism, Pathology and Behaviour in the 5XFAD Mouse Model pf Alzheimer's Disease," *Alzheimer's & Dimentia*9(4): Supplement:P246 (2013), Abstract.

Miyagi, T., "Aberrant expression of sialidase and cancer progression," *Proc. Jpn. Acad. Ser. B*, 2008, vol. 84, No. 10, pp. 407-418.

Miyagi, T., et al., "Multiple Forms of Mammalian Sialidase: Altered Expression in Carcinogenesis," *Tohoku J. Exp. Med.*, 1992, vol. 168, No. 2, pp. 223-229.

Miyagi, T., et al., "Human sialidase as a cancer marker," *Proteomics*, 2008, vol. 8, No. 16, pp. 3303-3311.

Miyagi, T., et al., "Sialidase and malignancy: A minireview," *Glycoconjugate Journal*, 2003, vol. 20, No. 3, pp. 189-198.

Proshin, S. N., et al., "Cells of Rhabdomyosarcoma Pa-23 Tumor Clones with High and Low Metastatic Potential Differ by Activity of Lysosomal Sialidase," *Bulletin of Experimental Biology and Medicine*, 2008, vol. 145, No. 3, pp. 355-357.

Tacko, M., et al., "Aberrant Expression of Sialidase in Cancer," *Trends in Glycoscience and Glyotechnology*, 2004, vol. 16, No. 92, pp. 371-381.

Uemura, T., et al., "Contribution of sialidase NEU1 to suppression of metastasis of human colon cancer cells through desialylation of integrin β4," *Oncogene*, 2009, vol. 28, pp. 1218-1229.

Wang, D., et al., "Short-term, high dose enzyme replacement therapy in sialidosis mice," *Molecular Genetics and Metabolism*, 2005, vol. 85, pp. 181-189.

Wells, J., et al., "Additivity of Mutational Effects in Proteins," *Biochemistry*, 1990, vol. 29(37), pp. 8509-8517.

Seffernick, J., et al., "Melamine Deaminase andAtrazine Cholorohydrolase: 98 Percent Identical but Functionally Different," *Journal Of Bacteriology*, 2001, vol. 183(8), pp. 2405-2410.

Yogalingam, G., et al., "Neuraminidase 1 Is a Negative Regulator of Lysosomal Exocytosis," *Developmental Cell*, 2008, vol. 15, pp. 74-86.

Figure 2

| Common proteins | Status in Sialidosis | Status in AD |
|---|---|---|
| Lamp1 | Increased in Neu1-/- brain and sialidosis patients | Increased in AD patients during progression of the disease (ref) |
| Cathepsin B | Increased in the CSF of Neu1-/- | High levels of Cathepsin B are found extracellular and associated with amyloid deposits (ref) |
| Cathepsin D | Increased in the CSF of Neu1-/- | High levels of Cathepsin D are found extracellular and associated with amyloid deposits (ref) |
| Complement system proteins | Increased in the CSF of Neu1-/- | Complement system plays a central role in the amplification of AD risk factors and neuronal death (ref) |
| Fibrinogen | All subunits of fibrinogen are increased in the CSF of Neu1-/- | Fibrinogen γ-A chain precursor protein is increased in CSF of AD patients |
| Hexosaminidase beta | Increased in the CSF of Neu1-/- | |
| Mannosidase alpha | Increased in the CSF of Neu1-/- | |
| Transthyretin | Increased in the CSF of Neu1-/- | Increased in CSF of AD (ref) |
| beta-2 microglobulin | Increased in the CSF of Neu1-/- | Increased in CSF of AD (ref) |
| Immunoglobulin heavy chains | Decreased in the CSF of Neu1-/- | Decreased in CSF of AD (ref) |

SEQUENCE LISTING

<160> NUMBER OF SEQ ID NOS: 4

<210> SEQ ID NO 1
<211> LENGTH: 1644
<212> TYPE: DNA
<213> ORGANISM: Homo sapiens
<220> FEATURE:
<221> NAME/KEY: misc_feature
<222> LOCATION: 1427
<223> OTHER INFORMATION: n = A,T,C or G

<400> SEQUENCE: 1

```
ccaagcttag atcttggagt ctagctgcca gggtcgcggc agctgcgggg agagatgact      60
ggggagcgac ccagcacggc gctcccggac agacgctggg ggccgcggat tctgggcttc     120
tggggaggct gtagggtttg ggtgtttgcc gcgatcttcc tgctgctgtc tctggcagcc     180
tcctggtcca aggctgagaa cgacttcggt ctggtgcagc cgctggtgac catggagcaa     240
ctgctgtggg tgagcgggag acagatcggc tcagtggaca ccttccgcat cccgctcatc     300
acagccactc cgcggggcac tcttctcgcc tttgctgagg cgaggaaaat gtcctcatcc     360 gatgagggggg ccaagttcat cgccctgcgg aggtccatgg accagggcag cacatggtct     420
cctacagcgt tcattgtcaa tgatgggggat gtccccgatg ggctgaacct ggggcagta      480 gtgagcgatg ttgagacagg agtagtattt ctttttctact ccctttgtgc tcacaaggcc     540
ggctgccagg tggcctctac catgttggta tggagcaagg atgatggtgt ttcctggagc     600
acaccccgga atctctccct ggatattggc actgaagtgt ttgcccctgg accgggctct     660
ggtattcaga aacagcggga gccacggaag ggccgcctca tcgtgtgtgg ccatgggacg     720
ctggagcggg acggagtctt ctgtctcctc agcgatgatc atggtgcctc ctggcgctac     780
ggaagtgggg tcagcggcat cccctacggt cagcccaagc aggaaaatga tttcaatcct     840
gatgaatgcc agccctatga gctcccagat ggctcagtcg tcatcaatgc ccgaaaccag     900
aacaactacc actgccactg ccgaattgtc ctccgcagct atgatgcctg tgatacacta     960
aggccccgtg atgtgacctt cgaccctgag ctcgtggacc ctgtggtagc tgcaggagct    1020
gtagtcacca gctccggcat tgtcttcttc tccaacccag cacatccaga gttccgagtg    1080
aacctgaccc tgcgatggag cttcagcaat ggtacctcat ggcggaaaga gacagtccag    1140
ctatggccag gccccagtgg ctattcatcc ctggcaaccc tggagggcag catggatgga    1200
gaggagcagg ccccccagct ctacgtcctg tatgagaaag gccggaacca ctacacagag    1260
agcatctccg tggccaaaat cagtgtctat gggacactct gagctgtgcc actgccacag    1320
gggtattctg ccttcaggac tctgccttca ggaagacggg tctgtagagg gtctgctgga    1380
gacgcctgaa agacagttcc atcttccttt agactccagc cttggcnaca tcaccttccc    1440
```

```
tttaccaggg aaatcacttc ctttaggact gaaagctagg cgtcctctcc cacaacaaag    1500
tcctgccctc atctgagaat actgtctttc catatggcta agtgtggccc caccaccctc    1560
tctgccctcc cgggacattg attggtcctg tcttgggcag gtctagtgag ctgtagaaat    1620
gaatcaatgt gaactcaggg aact                                            1644
```

<210> SEQ ID NO 2
<211> LENGTH: 415
<212> TYPE: PRT
<213> ORGANISM: Homo sapiens

<400> SEQUENCE: 2

```
Met Thr Gly Glu Arg Pro Ser Thr Ala Leu Pro Asp Arg Arg Trp Gly
 1               5                  10                  15

Pro Arg Ile Leu Gly Phe Trp Gly Gly Cys Arg Val Trp Val Phe Ala
             20                  25                  30

Ala Ile Phe Leu Leu Leu Ser Leu Ala Ala Ser Trp Ser Lys Ala Glu
         35                  40                  45

Asn Asp Phe Gly Leu Val Gln Pro Leu Val Thr Met Glu Gln Leu Leu
     50                  55                  60

Trp Val Ser Gly Arg Gln Ile Gly Ser Val Asp Thr Phe Arg Ile Pro
 65                  70                  75                  80

Leu Ile Thr Ala Thr Pro Arg Gly Thr Leu Leu Ala Phe Ala Glu Ala
                 85                  90                  95

Arg Lys Met Ser Ser Asp Glu Gly Ala Lys Phe Ile Ala Leu Arg
             100                 105                 110

Arg Ser Met Asp Gln Gly Ser Thr Trp Ser Pro Thr Ala Phe Ile Val
         115                 120                 125

Asn Asp Gly Asp Val Pro Asp Gly Leu Asn Leu Gly Ala Val Val Ser
     130                 135                 140

Asp Val Glu Thr Gly Val Val Phe Leu Phe Tyr Ser Leu Cys Ala His
145                 150                 155                 160

Lys Ala Gly Cys Gln Val Ala Ser Thr Met Leu Val Trp Ser Lys Asp
                 165                 170                 175

Asp Gly Val Ser Trp Ser Thr Pro Arg Asn Leu Ser Leu Asp Ile Gly
             180                 185                 190

Thr Glu Val Phe Ala Pro Gly Pro Gly Ser Gly Ile Gln Lys Gln Arg
         195                 200                 205

Glu Pro Arg Lys Gly Arg Leu Ile Val Cys Gly His Gly Thr Leu Glu
     210                 215                 220

Arg Asp Gly Val Phe Cys Leu Leu Ser Asp Asp His Gly Ala Ser Trp
225                 230                 235                 240

Arg Tyr Gly Ser Gly Val Ser Gly Ile Pro Tyr Gly Gln Pro Lys Gln
                 245                 250                 255

Glu Asn Asp Phe Asn Pro Asp Glu Cys Gln Pro Tyr Glu Leu Pro Asp
             260                 265                 270

Gly Ser Val Val Ile Asn Ala Arg Asn Gln Asn Asn Tyr His Cys His
         275                 280                 285

Cys Arg Ile Val Leu Arg Ser Tyr Asp Ala Cys Asp Thr Leu Arg Pro
     290                 295                 300

Arg Asp Val Thr Phe Asp Pro Glu Leu Val Asp Pro Val Val Ala Ala
305                 310                 315                 320

Gly Ala Val Val Thr Ser Ser Gly Ile Val Phe Phe Ser Asn Pro Ala
                 325                 330                 335
```

```
His Pro Glu Phe Arg Val Asn Leu Thr Leu Arg Trp Ser Phe Ser Asn
            340                 345                 350
Gly Thr Ser Trp Arg Lys Glu Thr Val Gln Leu Trp Pro Gly Pro Ser
        355                 360                 365
Gly Tyr Ser Ser Leu Ala Thr Leu Glu Gly Ser Met Asp Gly Glu Glu
    370                 375                 380
Gln Ala Pro Gln Leu Tyr Val Leu Tyr Glu Lys Gly Arg Asn His Tyr
385                 390                 395                 400
Thr Glu Ser Ile Ser Val Ala Lys Ile Ser Val Tyr Gly Thr Leu
                405                 410                 415
```

<210> SEQ ID NO 3
<211> LENGTH: 1815
<212> TYPE: DNA
<213> ORGANISM: Homo sapiens

<400> SEQUENCE: 3

| | | | | | |
|---|---|---|---|---|---|
| ggggagatga | tccgagccgc | gccgccgccg | ctgttcctgc | tgctgctgct | gctgctgctg | 60 |
| ctagtgtcct | gggcgtcccg | aggcgaggca | gcccccgacc | aggacgagat | ccagcgcctc | 120 |
| cccgggctgg | ccaagcagcc | gtctttccgc | cagtactccg | gctacctcaa | aagctccggc | 180 |
| tccaagcacc | tccactactg | gtttgtggag | tcccagaagg | atcccgagaa | cagccctgtg | 240 |
| gtgctttggc | tcaatggggg | tcccggctgc | agctcactag | atgggctcct | cacagagcat | 300 |
| ggccccttcc | tggtccagcc | agatggtgtc | accctggagt | acaaccccta | ttcttggaat | 360 |
| ctgattgcca | atgtgttata | cctggagtcc | ccagctgggg | tgggcttctc | ctactccgat | 420 |
| gacaagtttt | atgcaactaa | tgacactgag | gtcgcccaga | gcaattttga | ggcccttcaa | 480 |
| gatttcttcc | gcctctttcc | ggagtacaag | aacaacaaac | ttttcctgac | cggggagagc | 540 |
| tatgctggca | tctacatccc | caccctggcc | gtgctggtca | gcaggatcc | agcatgaac | 600 |
| cttcaggggc | tggctgtggg | caatggactc | tcctcctatg | agcagaatga | caactccctg | 660 |
| gtctactttg | cctactacca | tggccttctg | gggaacaggc | tttggtcttc | tctccagacc | 720 |
| cactgctgct | ctcaaaacaa | gtgtaacttc | tatgacaaca | aagacctgga | atgcgtgacc | 780 |
| aatcttcagg | aagtggcccg | catcgtgggc | aactctggcc | tcaacatcta | caatctctat | 840 |
| gccccgtgtg | ctggaggggt | gcccagccat | tttaggtatg | agaaggacac | tgttgtggtc | 900 |
| caggatttgg | gcaacatctt | cactcgcctg | ccactcaagc | ggatgtggca | tcaggcactg | 960 |
| ctgcgctcag | ggataaaagt | gcgcatggac | ccccctgca | ccaacacaac | agctgcttcc | 1020 |
| acctacctca | caacccgta | cgtgcggaag | gccctcaaca | tcccggagca | gctgccacaa | 1080 |
| tgggacatgt | gcaactttct | ggtaaactta | cagtaccgcc | gtctctaccg | aagcatgaac | 1140 |
| tcccagtatc | tgaagctgct | tagctcacag | aaataccaga | tcctattata | taatggagat | 1200 |
| gtagacatgg | cctgcaattt | catggggat | gagtggtttg | tggattccct | caaccagaag | 1260 |
| atggaggtgc | agcgccggcc | ctggttagtg | aagtacgggg | acagcgggga | gcagattgcc | 1320 |
| ggcttcgtga | aggagttctc | ccacatcgcc | tttctcacga | tcaagggcgc | cggccacatg | 1380 |
| gttcccaccg | acaagcccct | cgctgccttc | accatgttct | cccgcttcct | gaacaagcag | 1440 |
| ccatactgat | gaccacagca | accagctcca | cggcctgatg | cagcccctcc | cagcctctcc | 1500 |
| cgctaggaga | gtcctcttct | aagcaaagtg | ccctgcagg | cgggttctgc | cgccaggact | 1560 |
| gccccttcc | cagagccctg | tacatcccag | actgggccca | gggtctccca | tagacagcct | 1620 |
| gggggcaagt | tagcacttta | ttcccgcagc | agttcctgaa | tggggtggcc | tggccccttc | 1680 |

```
tctgcttaaa gaatgcccct tatgatgcac tgattccatc ccaggaaccc aacagagctc    1740
aggacagccc acaggaggt ggtggacgga ctgtaattga tagattgatt atggaattaa    1800
attgggtaca gcttc                                                    1815
```

<210> SEQ ID NO 4
<211> LENGTH: 480
<212> TYPE: PRT
<213> ORGANISM: Homo sapiens

<400> SEQUENCE: 4

```
Met Ile Arg Ala Ala Pro Pro Leu Phe Leu Leu Leu Leu Leu Leu
1               5                  10                  15

Leu Leu Leu Val Ser Trp Ala Ser Arg Gly Glu Ala Ala Pro Asp Gln
            20                  25                  30

Asp Glu Ile Gln Arg Leu Pro Gly Leu Ala Lys Gln Pro Ser Phe Arg
        35                  40                  45

Gln Tyr Ser Gly Tyr Leu Lys Ser Ser Gly Ser Lys His Leu His Tyr
    50                  55                  60

Trp Phe Val Glu Ser Gln Lys Asp Pro Glu Asn Ser Pro Val Val Leu
65                  70                  75                  80

Trp Leu Asn Gly Gly Pro Gly Cys Ser Ser Leu Asp Gly Leu Leu Thr
                85                  90                  95

Glu His Gly Pro Phe Leu Val Gln Pro Asp Gly Val Thr Leu Glu Tyr
            100                 105                 110

Asn Pro Tyr Ser Trp Asn Leu Ile Ala Asn Val Leu Tyr Leu Glu Ser
        115                 120                 125

Pro Ala Gly Val Gly Phe Ser Tyr Ser Asp Asp Lys Phe Tyr Ala Thr
    130                 135                 140

Asn Asp Thr Glu Val Ala Gln Ser Asn Phe Glu Ala Leu Gln Asp Phe
145                 150                 155                 160

Phe Arg Leu Phe Pro Glu Tyr Lys Asn Asn Lys Leu Phe Leu Thr Gly
                165                 170                 175

Glu Ser Tyr Ala Gly Ile Tyr Ile Pro Thr Leu Ala Val Leu Val Met
            180                 185                 190

Gln Asp Pro Ser Met Asn Leu Gln Gly Leu Ala Val Gly Asn Gly Leu
        195                 200                 205

Ser Ser Tyr Glu Gln Asn Asp Asn Ser Leu Val Tyr Phe Ala Tyr Tyr
    210                 215                 220

His Gly Leu Leu Gly Asn Arg Leu Trp Ser Ser Leu Gln Thr His Cys
225                 230                 235                 240

Cys Ser Gln Asn Lys Cys Asn Phe Tyr Asp Asn Lys Asp Leu Glu Cys
                245                 250                 255

Val Thr Asn Leu Gln Glu Val Ala Arg Ile Val Gly Asn Ser Gly Leu
            260                 265                 270

Asn Ile Tyr Asn Leu Tyr Ala Pro Cys Ala Gly Gly Val Pro Ser His
        275                 280                 285

Phe Arg Tyr Glu Lys Asp Thr Val Val Gln Asp Leu Gly Asn Ile
    290                 295                 300

Phe Thr Arg Leu Pro Leu Lys Arg Met Trp His Gln Ala Leu Leu Arg
305                 310                 315                 320

Ser Gly Asp Lys Val Arg Met Asp Pro Pro Cys Thr Asn Thr Thr Ala
                325                 330                 335

Ala Ser Thr Tyr Leu Asn Asn Pro Tyr Val Arg Lys Ala Leu Asn Ile
            340                 345                 350
```

```
Pro Glu Gln Leu Pro Gln Trp Asp Met Cys Asn Phe Leu Val Asn Leu
        355                 360                 365

Gln Tyr Arg Arg Leu Tyr Arg Ser Met Asn Ser Gln Tyr Leu Lys Leu
    370                 375                 380

Leu Ser Ser Gln Lys Tyr Gln Ile Leu Leu Tyr Asn Gly Asp Val Asp
385                 390                 395                 400

Met Ala Cys Asn Phe Met Gly Asp Glu Trp Phe Val Asp Ser Leu Asn
                405                 410                 415

Gln Lys Met Glu Val Gln Arg Arg Pro Trp Leu Val Lys Tyr Gly Asp
            420                 425                 430

Ser Gly Glu Gln Ile Ala Gly Phe Val Lys Glu Phe Ser His Ile Ala
        435                 440                 445

Phe Leu Thr Ile Lys Gly Ala Gly His Met Val Pro Thr Asp Lys Pro
    450                 455                 460

Leu Ala Ala Phe Thr Met Phe Ser Arg Phe Leu Asn Lys Gln Pro Tyr
465                 470                 475                 480
```

METHODS OF TREATING DEMENTIA ASSOCIATED WITH ALZHEIMER'S DISEASE WITH PROTECTIVE PROTEIN/CATHEPSIN A (PPCA)

CROSS REFERENCE TO RELATED APPLICATIONS

This application is a continuation of U.S. patent application Ser. No. 15/187,349, filed Jun. 20, 2016, issued as U.S. Pat. No. 9,840,727 on Dec. 12, 2017, which is a continuation of U.S. patent application Ser. No. 14/239,728, filed Feb. 19, 2014, issued as U.S. Pat. No. 9,399,791 on Jul. 26, 2016, which is a National Stage Application of PCT/US2012/052629, filed Aug. 28, 2012, which claims the benefit of U.S. Provisional Application Ser. No. 61/544,855, filed Oct. 7, 2011, and U.S. Provisional Application Ser. No. 61/529,675, filed Aug. 31, 2011. Each of these priority applications is incorporated herein by reference in their entirety.

FEDERALLY SPONSORED RESEARCH OR DEVELOPMENT

This invention was made with Federal Government support under GM060950 awarded by the National Institutes of Health. The United States Government has certain rights in the invention. This invention was also supported by the American Lebanese Syrian Associated Charities (ALSAC) of St. Jude Children's Research Hospital.

FIELD OF THE INVENTION

The present invention relates to the field of molecular biology, cancer and Alzheimer's disease therapeutics and diagnostics.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 423475SEQLIST.txt, a creation date of Aug. 22, 2012, and a size of 13 KB. The sequence listing filed via EFS-Web is part of the specification and is hereby incorporated in its entirety by reference herein.

BACKGROUND OF THE INVENTION

The prognosis of a disease or pathological condition in a subject can be greatly improved with an early diagnosis. However, reliable prognostic and diagnostic methods are lacking for managing disease states. For example, for Alzheimer's disease, the only definitive diagnostic test is to determine whether amyloid plaques are present in a subject's brain tissue, a determination that can only be made after death. Thus, due to the lack of suitable diagnostic methods only a tentative diagnosis can be provided. In another example, diagnosis and prognosis of a cancer are important for choosing the best treatment options in order to improve outcome. There is also a need for diagnostic and prognostic tests to predict the efficacy of a particular chemotherapy regime to determine the best treatment options for a subject.

Therefore, there is a significant need in the art for more accurate and reliable diagnostic and prognostic methods for cancer and Alzheimer's disease.

BRIEF SUMMARY OF THE INVENTION

Methods are provided for the prognosis, diagnosis and treatment of various pathological states, including cancer, chemotherapy resistance and dementia associated with Alzheimer's disease. The methods provided herein are based on the discovery that various proteins with a high level of sialylation are shown herein to be associated with disease states, such as, cancer, chemotherapy resistance and dementia associated with Alzheimer's disease. Such methods provide a lysosomal exocytosis activity profile comprising one or more values representing lysosomal exocytosis activity. Also provided herein, is the discovery that low lysosomal sialidase activity is associated with various pathological states. Thus, the methods also provide a lysosomal sialidase activity profile, comprising one or more values representing lysosomal sialidase activity. A lysosomal sialidase activity profile is one example of a lysosomal exocytosis activity profile. As such, the level of lysosomal exocytosis activity and/or lysosomal sialidase activity is predictive of a diagnosis and/or prognosis of cancer, chemotherapy resistance or dementia associated with Alzheimer's disease.

BRIEF DESCRIPTION OF THE DRAWINGS

FIG. 2 depicts the presence of lysosomal proteins in the CSF and the correlation of these proteins with Alzheimer's disease.

DETAILED DESCRIPTION OF THE INVENTION

Figure 1:
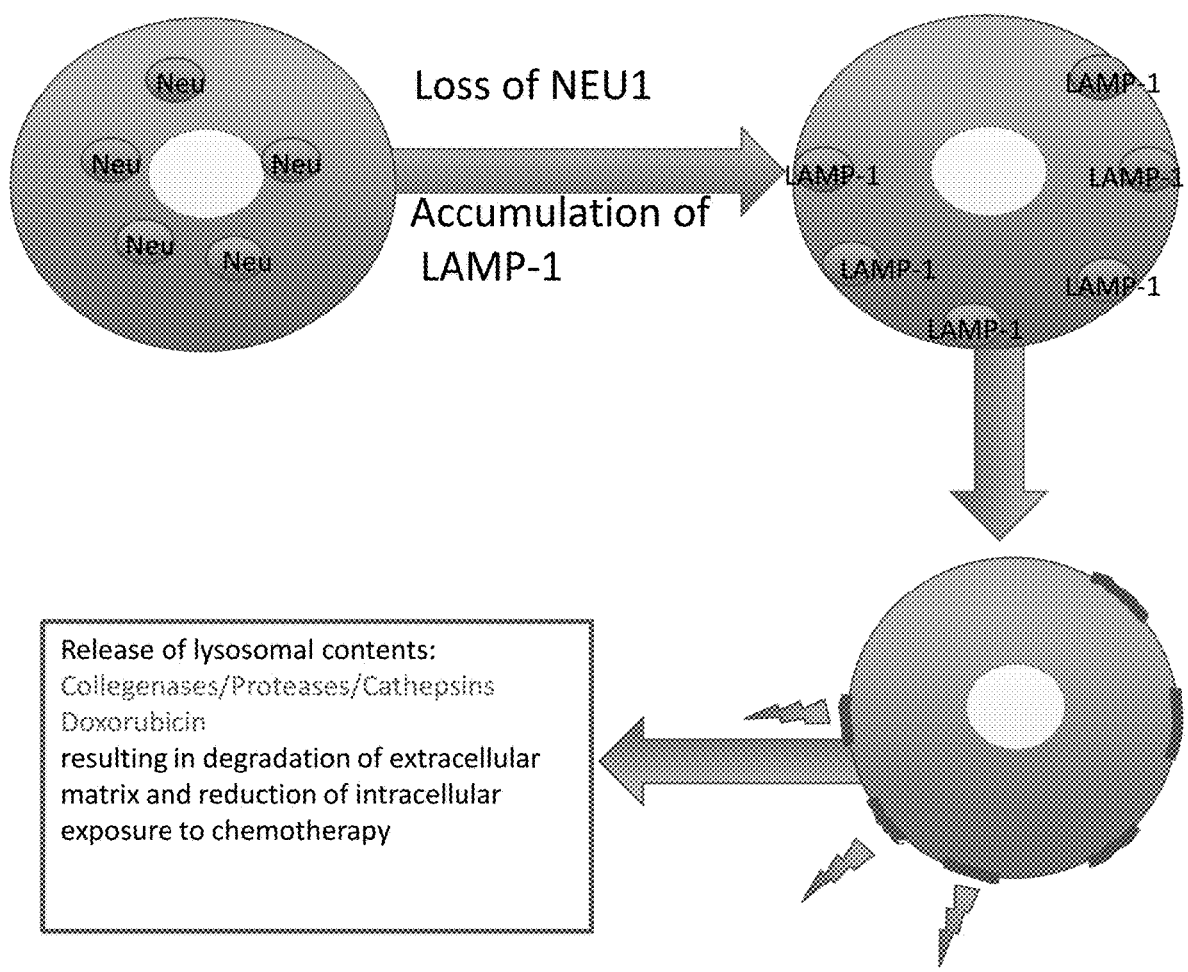
FIG. 1 displays a summary model of the role of NEU1 in cancer.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Provided herein are methods for the diagnosis and prognosis of various pathological states by looking at the lysosomal exocytosis activity in a sample. The level of lysosomal exocytosis activity can serve as a marker for the diagnosis and/or prognosis of pathological conditions including, for example, cancer, chemotherapy resistance and dementia associated with Alzheimer's disease. Various activity profiles are provided herein for the diagnosis and/or prognosis of cancer, chemotherapy resistance, and dementia associated with Alzheimer's disease.

II. Types of Profiles

As used herein, a "profile" comprises one or more values corresponding to a measurement of a marker(s) representing an activity in a sample. Various profiles are disclosed herein which can be used for the prognosis and/or diagnosis of a given pathological state. Such profiles include: a lysosomal exocytosis activity profile, a sialylation activity profile, a lysosomal sialidase activity profile, a NEU1 substrate sialylation activity profile and a NEU1 level activity profile. Each of these profiles is explained in detail herein and summarized in Table 1 herewith.

By "lysosomal exocytosis activity profile" is meant a profile of one or more values representing lysosomal exocytosis activity. As used herein, "lysosomal exocytosis activity" is meant a measure of the level of exocytosis in a sample. Various markers can be used to determine the lysosomal exocytosis activity of a sample. Such markers include one or more of the following: (1) the level of NEU1 protein or direct enzymatic activity of NEU1; (2) the protein level of one or more NEU1 substrates; (3) the protein level of one or more lysosomal proteins; (4) the protein level of one or more lysosomal proteases; (5) the protein level of LAMP-1; (6) the protein level of hexosaminidase beta; (7) the protein level of mannosidase alpha; or (8) the protein level of one or more cathepsins; (9) any marker for a sialylation activity profile provided herein; or (10) any marker for a lysosomal sialidase activity profile provided herein. Once the level of each of a given marker is determined, it becomes a value in the lysosomal exocytosis activity profile. The lysosomal exocytosis activity profile can comprise 1, 2, 3, 4, 5, 6, 7, 8, 9, 10, 11, 12, 13, 14, 15 or more lysosomal exocytosis activity values of the various lysosomal exocytosis activity markers provided herein.

In one embodiment, one type of lysosomal exocytosis activity profile is a sialylation activity profile. By "sialylation activity profile" is meant a profile of one or more values representing sialylation activity. As used herein, "sialylation activity" is meant a measure of the sialylation level of a population of proteins in a sample or the sialylation level of one or more proteins in a sample. Various markers can be used to determine sialylation activity. Such markers include one or more of the following: (1) the overall level of sialylation in a sample; (2) the level of NEU1 protein or direct enzymatic activity of NEU1; (3) the level of sialylation of one or more NEU1 substrates; (4) the protein level of one or more NEU1 substrates; or (5) any marker for a lysosomal sialidase activity profile, as discussed in further detail elsewhere herein or outlined in Table 1. Once the level of each of a given marker is determined, it becomes a value in the sialylation activity profile. The sialylation activity profile can comprise 1, 2, 3, 4, 5, 6, 7, 8, 9, 10, 11, 12, 13, 14, 15 or more sialylation activity values of the various sialylation activity markers provided herein.

In one embodiment, one type of sialylation activity profile is a lysosomal sialidase activity profile. By "lysosomal sialidase activity profile" is meant a profile of one or more values representing lysosomal sialidase activity. By "lysosomal sialidase activity" is meant a direct or indirect measure of lysosomal sialidase activity. Various markers can be used to determine lysosomal sialidase activity in a sample. The various markers representing the lysosomal sialidase activity in a sample include any one or more of the following: (1) the level of NEU1 protein or the level of direct enzymatic activity of NEU1; (2) the protein level of one or more NEU1 substrate; (3) the level of sialylation of one or more NEU1 substrate; or (4) the activity level of one or more NEU1 substrate. Once the level or activity of a given marker is determined, it becomes a value in the lysosomal sialidase activity profile. Thus, the lysosomal sialidase activity profile can comprise any combination of the lysosomal sialidase activity markers provided herein. The lysosomal sialidase activity profile can comprise 1, 2, 3, 4, 5, 6, 7, 8, 9, 10, 11, 12, 13, 14, 15 or more lysosomal sialidase activity values of the various lysosomal sialidase activity markers provided herein.

In one embodiment, one type of lysosomal sialidase activity profile is a NEU1 substrate sialylation activity profile. By "NEU1 substrate sialylation activity profile" is meant measuring lysosomal sialidase activity in a sample by determining the level of sialylation of one or more NEU1 substrates. The various markers representing lysosomal sialidase activity that are encompassed in a NEU1 substrate sialylation activity profile include: (1) the level of sialylation of one or more NEU1 substrate; (2) the level of sialylation of LAMP-1; (3) The level of sialylation of MUC-1; or (4) the level of sialylation of NEU1 and MUC-1. The NEU1 substrate sialylation activity profile can comprise 1, 2, 3, 4, 5, 6, 7, 8, 9, 10, 11, 12, 13, 14, 15 or more marker values provided by the sialylation level of the various NEU1 substrates.

In another embodiment, one type of lysosomal sialidase activity profile is a NEU1 level activity profile. By "NEU1 level activity profile" is meant measuring lysosomal sialidase activity in a sample by determining the protein level of any non-MUC-1 NEU1 substrate or of NEU1 itself. The various markers representing lysosomal sialidase activity that are encompassed in a NEU1 level activity profile include: (1) the level of NEU1 protein; (2) the protein level of any one or more non-MUC-1 NEU1 substrate; or (3) the protein level of LAMP-1. The NEU1 level activity profile can comprise 1, 2, 3, 4, 5, 6, 7, 8, 9, 10, 11, 12, 13, 14, 15 or more marker values provided by the protein level of the various NEU1 substrates.

If multiple markers are present in a given profile, not all the markers must show an altered activity as compared to the marker value in a corresponding control or reference profile in order to produce the prognosis and/or diagnosis provided herein. In some instances, the alteration of a single marker may be sufficient for a diagnosis and/or prognosis. In other embodiments, an alteration in 2, 3, 4, 5, 6, 7, 8, 9, 10 or more marker values in a given profile as compared to the values in corresponding control or reference profile is sufficient for a diagnosis and/or prognosis.

TABLE 1

Summary of various markers employed to establish a specific type of activity profile.

| Marker | Lysosomal Exocytosis Activity Profile | Sialylation Activity Profile | Lysosomal Sialidase Activity Profile | NEU1 Substrate Sialylation Activity Profile | NEU1 Level Activity Profile |
|---|---|---|---|---|---|
| the level of NEU1 protein | + | + | + | | + |
| the level of direct enzymatic activity of NEU1 | + | + | + | | |
| the protein level of one or more NEU1 substrates | + | + | + | | + <br> At least one NEU1 substrate other than MUC-1 must be detected |
| the protein level of LAMP-1 | + | + | + | | + |
| the protein level of MUC-1 | + | + | + | | + <br> Only in combination with another NEU1 substrate |
| the protein level of LAMP-1 and MUC-1 | + | + | + | | + |
| the level of any one or more lysosomal proteins | + | | | | |
| the protein level of one or more lysosomal proteases | + | | | | |
| the protein level of one or more cathepsins | + | | | | |
| the protein level of Hexosaminidase beta | + | | | | |
| the protein level of mannosidase alpha | + | | | | |
| the activity level of one or more NEU1 substrates | + | + | + | | |
| the activity level of LAMP-1 | + | + | + | | |
| the activity level of MUC-1 | + | + | + | | |
| the activity level of LAMP-1 and MUC-1 | + | + | + | | |
| the overall level of sialylation in a sample | + | + | | | |
| the sialylation level of a NEU1 substrate (including levels of a population of substrates and/or the levels of a single substrate) | + | + | + | + | |
| the sialylation level of LAMP-1 | + | + | + | + | |
| the sialylation level of MUC-1 | + | + | + | + | |
| the sialylation level of LAMP-1 and MUC-1 | + | + | + | + | |
| the protein level and the sialylation level of one or more NEU1 substrates | + | + | + | | |
| the level of NEU1 protein, the protein level of one or more NEU1 substrates and the sialylation level of one or more NEU1 substrates | + | + | + | | |

TABLE 1-continued

Summary of various markers employed to establish a specific type of activity profile.

| Marker | Lysosomal Exocytosis Activity Profile | Sialylation Activity Profile | Lysosomal Sialidase Activity Profile | NEU1 Substrate Sialylation Activity Profile | NEU1 Level Activity Profile |
|---|---|---|---|---|---|
| the level of NEU1 protein, the level of NEU1 enzymatic activity, the protein level of one or more NEU1 substrates and the sialylation level of one or more NEU1 substrates | + | + | + | | |

III. Assays for Markers of the Various Activity Profiles

The methods for diagnosis and/or prognosis provided herein are based on analyzing a sample for lysosomal exocytosis activity, sialylation activity, lysosomal sialidase activity, NEU1 substrate sialylation activity and/or NEU1 level activity and comparing it to a reference value for lysosomal exocytosis activity, sialylation activity, lysosomal sialidase activity, NEU1 substrate sialylation activity and/or NEU1 level activity from a control sample. Measuring the "level" or "amount" of a protein, sialylation, or an activity in a sample means quantifying the lysosomal exocytosis activity, sialylation activity, lysosomal sialidase activity, NEU1 substrate sialylation activity or NEU1 level activity by determining, for example, the relative or absolute amount of protein and/or sialylation of a protein and/or the activity of a protein. One aspect of the methods provided herein relates to assays for detecting lysosomal exocytosis activity, sialylation activity, lysosomal sialidase activity, NEU1 substrate sialylation activity and NEU1 level activity in the context of a sample. These assays determine the values that make up the lysosomal exocytosis activity profile, sialylation activity profile, lysosomal sialidase activity profile, NEU1 substrate sialylation activity profile or NEU1 level activity profile of a sample.

A "sample" or "subject sample", as used herein, can comprise any sample in which one desires to determine the lysosomal exocytosis activity, sialylation activity, lysosomal sialidase activity, NEU1 substrate sialylation activity and/or NEU1 level activity. By "subject" is intended any animal (i.e. mammals) such as, humans, primates, rodents, agricultural and domesticated animals such as, but not limited to, dogs, cats, cattle, horses, pigs, sheep, and the like, in which one desires to determine the lysosomal exocytosis activity, sialylation activity and/or lysosomal sialidase activity. The sample may be derived from any cell, tissue, or biological fluid from the animal of interest. The sample may comprise any clinically relevant tissue, such as, but not limited to, bone marrow, cerebrospinal fluid, tumor biopsy, fine needle aspirate, or a sample of body fluid, such as blood, plasma, serum, lymph, ascetic fluid, cystic fluid or urine. The sample used in the methods provided herein will vary based on the assay format, nature of the detection method, and the tissues, cells or extracts which are used as the sample.

A "reference" lysosomal exocytosis activity, sialylation activity, lysosomal sialidase activity, NEU1 substrate sialylation activity and/or NEU1 level activity as used herein is provided in a control sample. A "control" or "control sample" provides a reference point for measuring changes in lysosomal exocytosis activity, sialylation activity, lysosomal sialidase activity, NEU1 substrate sialylation level activity and/or NEU1 level activity of a subject sample. The control may be a predetermined value based on a group of samples or it may be a single value based on an individual sample. The control may be a sample tested in parallel with the subject sample. A control sample may comprise, for example: (a) any sample from healthy individual(s); (b) a normal tissue sample taken from a location adjacent to a tumor from the same subject; (c) a tissue sample from healthy individual(s) taken from the same tissue type as a subject tumor; (c) a serum or plasma sample taken from healthy individual(s); (d) a cerebrospinal fluid sample taken from healthy individual(s); or (e) a urine sample from healthy individual(s).

As used herein a "higher" or "increased" level for a given marker (i.e. any of the various markers provided herein) is meant any significant increase in the level of the marker in a sample as compared to the level of the corresponding marker in a control sample. An increased or higher level for a given marker can be any statistically significant increase in the level of the marker of at least 5%, 10%, 15%, 20%, 25%, 30%, 40%, 50%, 60%, 70%, 80%, 85%, 90%, 95%, 96%, 97%, 98%, 99%, 100%, 200%, 400% or more as compared to a reference level in a control sample. Alternatively, an increase in the level for a given marker can be any fold increase of at least 1.5-fold, 2-fold, 3-fold, 4-fold, 5-fold, 6-fold, 7-fold, 8-fold, 9-fold, 10-fold, 12-fold, 14-fold, 16-fold, 20-fold or more over the value for the level of the corresponding marker in a control sample. In some embodiments, an increase in the level of a given marker can result in an increase in a specific activity in the sample (i.e. the lysosomal exocytosis activity, sialylation activity, lysosomal sialidase activity, NEU1 substrate sialylation activity or NEU1 level activity). In other embodiments, an increase in the level of a given marker can result in a decrease in a specific activity in a sample.

As used herein, a "decreased", "lower" or "reduced" level for a given marker (i.e. any of the various markers provided herein) is meant any significant decrease in the level of the marker in a sample as compared to the level of the corresponding marker in a control sample. By lower or reduced level of a marker is meant a statistically significant reduction in the level of a marker in a subject sample of at least 5%, 10%, 15%, 20%, 25%, 30%, 40%, 50%, 60%, 70%, 80%, 85%, 90%, 95%, 96%, 97%, 98%, 99% or more as compared to a reference level in a control sample. Alternatively, a decrease in the level for a given marker can be any fold decrease of at least 1.5-fold, 2-fold, 3-fold, 4-fold, 5-fold, 6-fold, 7-fold, 8-fold, 9-fold, 10-fold, 12-fold, 14-fold, 16-fold, 20-fold or more as compared to the level of the corresponding marker in a control sample. In some embodiments, a decrease in the level of a given marker can result in a decrease in a specific activity in the sample (i.e. the lysosomal exocytosis activity, sialylation activity, lysosomal sialidase activity, NEU1 substrate sialylation activity or NEU1 level activity). In other embodiments, a decrease in the level of a given marker can result in an increase in a specific activity in the sample.

Table 2 provides non-limiting examples of markers for the various activity profiles provided herein and denotes if an increase or a decrease in the marker is reflective of an increase or a decrease in the activity in a sample (i.e. the lysosomal exocytosis activity, sialylation activity, lysosomal sialidase activity, NEU1 substrate sialylation activity or NEU1 level activity).

A. Lysosomal Exocytosis Activity

In one embodiment, the lysosomal exocytosis activity of one or more lysosomal exocytosis activity markers in a sample is provided. As used herein, "exocytosis" is a process of cellular secretion in which substances contained in vesicles are discharged from the cell by fusion of the vesicular membrane with the outer cell membrane. There are two types of exocytosis, constitutive and regulated. Constitutive exocytosis is not regulated by calcium, while regulated exocytosis is dependent on calcium. Exocytosis involves vesicle recruitment, tethering and docking of the vesicle to the plasma membrane and fusion of the vesicle membrane with the plasma membrane thereby releasing the contents of the vesicle into the extracellular space. During exocytosis, the vesicles release various components into the extracellular environment. Some examples of components of secretory vesicles include, but are not limited to, enzymes, proteases, extracellular matrix components, hormones, neurotransmitters and cytotoxic compounds.

Lysosomal exocytosis is one type of exocytosis. By "lysosomal exocytosis" is meant the process by which lysosomes release their contents to the extracellular space. Lysosomal exocytosis is a calcium dependent process that involves the recruitment and docking of lysosomes to the plasma membrane, fusion of the lysosomal membrane with the plasma membrane and the release of lysosomal luminal content into the extracellular environment. Some examples of lysosomal contents include, but are not limited to, enzymes, such as lipases, proteases, nucleases and amylase, and other proteins related to lysosomal function, such as sialidases and proteins involved in lysosomal exocytosis.

In one embodiment, a subject sample has a higher or increased lysosomal exocytosis activity as compared to a control sample. By "higher lysosomal exocytosis activity" or "increased lysosomal exocytosis activity" is meant a statistically significant alteration in the level of one or more markers in the lysosomal exocytosis activity profile. Table 2 provides non-limiting examples of markers for the lysosomal exocytosis activity profile and denotes if an increase or a decrease in the marker is reflective of a higher lysosomal exocytosis activity.

In one embodiment, an increase in lysosomal exocytosis activity is denoted in a given profile by an alteration in at least 1, 2, 3, 4, 5, 6, 7, 8, 9, 10, 11, 12, 13, 14, 15 or all of the lysosomal exocytosis activity markers as compared to a control sample. In some cases, an alteration in lysosomal exocytosis activity of one marker is sufficient for a diagnosis and/or prognosis. In other cases an alteration in two or more lysosomal exocytosis activity markers is sufficient for a diagnosis and/or prognosis.

Assays to measure lysosomal exocytosis activity for an exocytosis marker are provided herein. One measure of lysosomal exocytosis activity is the level of a protein in a sample (i.e. NEU1, NEU1 substrates or lysosomal proteins). A variety of assays for detecting protein in a sample are known in the art and include direct and indirect assays for protein. An exemplary method for detecting the presence or absence or the quantity of a protein in a sample involves obtaining a sample and contacting the sample with a compound or agent capable of specifically binding and detecting the protein, such that the presence of the protein is detected in the sample. Results obtained with a sample from a subject may be compared to results obtained with a biological sample from a control subject.

In one embodiment, an agent for detecting a protein is an antibody capable of specifically binding to that protein. Antibodies can be polyclonal or monoclonal. The term "labeled", with regard to the antibody is intended to encompass direct labeling of the antibody by coupling (i.e. physically linking) a detectable substance to the antibody as well as indirect labeling of the antibody by reactivity with another reagent that is directly labeled. Examples of indirect labeling include detection of a primary antibody using a fluorescently labeled secondary antibody.

The level of a protein in a sample can be quantitatively measured by a variety of assays utilizing antibodies for a specific protein. These include, for example, immunoassays, radioimmunoassays, enzyme-linked immunosorbant assays and two-antibody sandwich assays. Quantitative western blotting can also be used to determine the level of protein. Western blots can be quantitated by well-known methods such as scanning densitometry. In addition, antibodies can be used to detect and quantitate the level of protein in a sample of a tissue by fluorescence or confocal microscopy by using a fluorescently labeled antibody or secondary reagent.

In another embodiment, a marker is the level of sialylation of a sample. Assays for measuring the level of sialylation in a sample are provided elsewhere herein, for example, in the section on sialylation activity.

In yet another embodiment, a marker is the level of protein activity in a sample. The protein activity for any protein provided herein can be measured by assaying for the activity of the specific protein in a sample. For example, if the protein is an enzyme, the activity of the enzyme can be measured in an enzyme activity assay. Various assays are known in the art for measuring enzymatic activity. For example, NEU1 enzyme activity in a sample can be measured by incubating the sample with a sialylated NEU1 substrate and detecting the amount of free sialic acid present in the sample after incubation. As such, the units of enzyme activity can be calculated (i.e. the amount of activity per milligram of protein).

B. Sialylation Activity

In one embodiment, the sialylation activity of one or more sialylation activity markers in a sample is provided. As used herein, a protein or lipid is "sialylated" if a sialic acid is present on the terminal portion of a glycoprotein or glycolipid. By "sialylation" is meant the transfer of sialic acid to the terminal portions of the sialylated glycolipids or to the N- or O-linked sugar chains of glycoproteins. Sialylation can be catalyzed by a number of different sialyltransferases, each with specificity for a particular sugar substrate. Non-limiting examples of sialyltransferases known in the art include, for example, sialyltransferase, beta-galactosamide alpha-2,6-sialyltransferase, alpha-N-acetylgalactosaminide alpha-2,6-sialyltransferase, beta-galactoside alpha-2,3-sialyltransferase, N-acetyllactosaminide alpha-2,3-sialyltransferase, alpha-N-acetyl-neuraminide alpha-2,8-sialyltransferase and lactosylceramide alpha-2,3-sialyltransferase.

Sialyltransferases can transfer sialic acid to a substrate by various linkages. For example, some sialyltransferases add sialic acid with an alpha-2,3 linkage to galactose, while other sialyltransferases add sialic acid with an alpha-2,6 linkage to galactose or N-acetylgalactosamine. Another group of sialyltransferases can add sialic acid to other sialic acids by an alpha-2,8 linkage. In one embodiment, the sialic acid is added with an alpha-2,6 linkage to a glycoprotein. In another embodiment, the sialic acid is added with an alpha 2,3 linkage to a glycoprotein.

In one embodiment, a subject sample has a higher or increased sialylation activity as compared to a control sample. By "higher sialylation activity" or "increased sialylation activity" is meant a statistically significant alteration in the level of one or more markers in the sialylation activity profile. Table 2 provides non-limiting examples of markers for the sialylation activity profile and denotes if an increase or a decrease in the marker is reflective of a higher sialylation activity.

In one embodiment, an increase in sialylation activity is denoted in a given profile by an alteration in at least 1, 2, 3, 4, 5, 6, 7, 8, 9, 10, 11, 12, 13, 14, 15 or all of the sialylation activity markers as compared to a control sample. In some cases, an alteration in sialylation activity of one marker is sufficient for a diagnosis and/or prognosis. In other cases an alteration in two or more sialylation activity markers is sufficient for a diagnosis and/or prognosis.

Various assays are known to measure sialylation levels in a sample. For example, a sample can be incubated with sambuscus nigra lectin (SNA) that binds preferentially to sialic acid attached to a terminal galactose in position alpha-2,6. Other assays for sialylation are known in the art and include the use of Machia amurentis lectin that binds sialic acids attached with an alpha-2,3 linkage.

In one embodiment, sialylation activity can be measured for a population of proteins to determine global sialylation of proteins in a sample. For example, sialylation in this context can be assayed for in a sample by lectin binding assays. The lectin binding assays can be ELISA based or can be gel based. In another embodiment, the sialylation activity of a single protein can be measured. In this instance, an ELISA based or gel based lectin assay can be coupled with a specific antibody to a protein of interest. The level of sialylation in a sample can be quantitated by using samples of known different sialylation levels as standards in the assay.

C. Lysosomal Sialidase Activity

In one embodiment, the sialylation activity comprises the level of lysosomal sialidase activity. "Sialidases" are enzymes that remove the terminal sialic acid from glycoproteins by a process called desialylation. In mammals, there are at least four types of sialidases including, for example, Neuraminidase 1 (NEU1), NEU2, NEU3 and NEU4 which differ in substrate specificity and subcellular localization. NEU1, for example, is localized to the lysosome and cleaves terminal sialic acid residues from substrates such as glycoproteins. As such, NEU1 is an enzyme that contributes to the overall sialylation activity of a sample.

In the lysosome, NEU1 is part of a heterotrimeric complex together with beta-galactosidase and protective protein/cathepsin A (PPCA). The presence of PPCA in the NEU1 complex stabilizes NEU1 in the lysosome. NEU1 has various substrates. As used herein, a "NEU1 substrate" is any protein that is desialylated by NEU1. Some non-limiting examples of NEU1 substrates include LAMP-1, Cathepsin A, mucins (i.e. MUC1), cathepsin D, cathepsin B and Amyloid Precursor Protein. NEU1 can catalyze the hydrolysis of alpha 2-3 and alpha 2-6 sialyl linkages of terminal sialic acid residues in oligosaccharides, glycoproteins and glycolipids. Desialylation of a glycoprotein, for example, leads to the destabilization and degradation of the protein. Thus, the sialidase, NEU1, contributes to the turnover of glycoproteins.

In addition to its role as a sialidase, NEU1 has a related effect on the constitutive process of lysosomal exocytosis. As described elsewhere herein, lysosomal exocytosis involves the recruitment and docking of lysosomes to the plasma membrane, fusion of the lysosomal membrane with the plasma membrane and the release of lysosomal luminal content into the extracellular environment. The recruitment and docking step is facilitated by the lysosomal associated protein-1 (LAMP-1). LAMP-1 is a NEU1 substrate, and thus the stability and turnover rate of LAMP-1 can be influenced by lysosomal sialidase activity.

In one embodiment, a subject sample has a lower or decreased lysosomal sialidase activity as compared to a control sample. By "lower lysosomal sialidase activity" or "decreased lysosomal sialidase activity" is meant a statistically significant alteration in the level of one or more markers in the lysosomal sialidase activity profile. Table 2 provides non-limiting examples of markers for the lysosomal sialidase activity profile and denotes if an increase or a decrease in the marker is reflective of a lower lysosomal sialidase activity.

In one embodiment, a decrease in lysosomal sialidase activity is denoted in a given profile by an alteration in at least 1, 2, 3, 4, 5, 6, 7, 8, 9, 10, 11, 12, 13, 14, 15 or all of the lysosomal sialidase activity markers as compared to a control sample. In some cases, an alteration in lysosomal sialidase activity of one marker is sufficient for a diagnosis and/or prognosis. In other cases, an alteration in two or more lysosomal sialidase activity markers is sufficient for a diagnosis and/or prognosis.

In one embodiment, lysosomal sialidase activity is measured by the level of NEU1 protein or enzymatic activity of NEU1. Assays to measure NEU1 protein level are well known in the art and include contacting a sample with an antibody to NEU1. In addition, NEU1 enzymatic activity can be measured directly in a sample by assaying for NEU1 enzyme activity of a sample in the presence of a sialylated NEU1 substrate. Thus, when NEU1 protein and/or enzyme activity levels in a sample are low or absent, NEU1 substrates will not be desialylated or will be desialylated at a lower rate resulting in an increase in sialylation of the substrate and/or an increase in the stability of the substrate and thus an increase in the protein level of the NEU1 substrate in a sample. For example, under conditions where NEU1 protein is not present in a sample (i.e. in a NEU1 knockout), LAMP-1 is over-sialylated, accumulates in the lysosome, recruits the lysosome to the plasma membrane and facilitates docking of the lysosome to the plasma membrane. In such cases, the loss of NEU1 protein/activity results in an increase in lysosomal exocytosis.

As used herein, an increase in sialylation of any one or more NEU1 substrates results in a lower lysosomal sialidase activity in a sample. Further, an increase in the protein level of any one or more of the NEU1 substrates provided herein also results in a lower lysosomal sialidase activity. As such, these values are markers for lysosomal sialidase activity and indicative of low protein and activity levels of NEU1 in a sample. Assays to measure for sialylation levels in a sample or the sialylation level of a specific protein in a sample are discussed elsewhere herein. Assays to measure the protein level of any of the various lysosomal sialidase activity markers are known in the art and are described in detail elsewhere herein.

In another embodiment, the enzymatic activity level of NEU1 or the activity level of any of the various NEU1 substrates are markers for lysosomal sialidase activity. Assays to measure the protein activity for various proteins is known in the art and described elsewhere herein.

D. NEU1 Substrate Sialylation Activity

In one embodiment, one type of lysosomal sialidase profile is a NEU1 substrate sialylation activity profile. Non-limiting examples of the various NEU1 substrate sialylation activity markers are summarized in Table 1.

In one embodiment, a subject sample has a higher or increased NEU1 substrate sialylation activity as compared to a control sample. By "higher NEU1 substrate sialylation activity" or "increased NEU1 substrate sialylation activity" is meant a statistically significant alteration in the level of one or more markers in the NEU1 substrate sialylation activity profile. Table 2 provides non-limiting examples of markers for the NEU1 substrate sialylation activity profile and denotes if an increase or a decrease in the marker is reflective of a higher NEU1 substrate sialylation activity.

In one embodiment, an increase in NEU1 substrate sialylation activity is denoted in a given profile by an alteration in at least 1, 2, 3, 4, 5, 6, 7, 8, 9, 10, 11, 12, 13, 14, 15 or all of the NEU1 substrate sialylation activity markers as compared to a control sample. In some cases, an alteration in NEU1 substrate sialylation activity of one marker is sufficient for a diagnosis and/or prognosis. In other cases an alteration in two or more NEU1 substrate sialylation activity markers is sufficient for a diagnosis and/or prognosis.

Assays to measure the NEU1 substrate sialylation activity of the various NEU1 substrate sialylation activity markers are known in the art and include measuring the level of sialylation of any of the various NEU1 substrates provided herein. Such assays are described elsewhere herein.

E. NEU1 Level Activity

In another embodiment, one type of lysosomal sialidase activity profile is a NEU1 level activity profile. Non-limiting examples of the various NEU1 level activity markers are summarized in Table 1.

In one embodiment, a subject sample has a higher or increased NEU1 level activity as compared to a control sample. By "higher NEU1 level activity" or "increased NEU1 level activity" is meant a statistically significant alteration in the level of two or more markers in the NEU1 level activity profile. Table 2 provides non-limiting examples of markers for the NEU1 level activity profile and denotes if an increase or a decrease in the marker is reflective of a higher NEU1 level activity.

In one embodiment, an increase in NEU1 level activity is denoted in a given profile by an alteration in at least 2, 3, 4, 5, 6, 7, 8, 9, 10, 11, 12, 13, 14, 15 or all of the NEU1 level activity markers as compared to a control sample. In some cases, an alteration in NEU1 level activity of two or more markers is sufficient for a diagnosis and/or prognosis.

Assays to measure NEU1 level activity of the various NEU1 level activity markers are known in the art and include, for example, immuno-blotting using an antibody specific for a NEU1 level activity marker or ELISA assay using an antibody specific for a NEU1 level activity marker. These assays are discussed in detail elsewhere herein.

TABLE 2

Summary of alterations in various markers employed to establish an increase or decrease in a specific type of activity.

| Marker | Level of Marker Compared to Control |
|---|---|
| Increased Lysosomal exocytosis activity | |
| the level of NEU1 protein | Decreased |
| the level of NEU1 enzymatic activity | Decreased |
| the protein level of one or more NEU1 substrates | Increased |
| the protein level of LAMP-1 | Increased |
| the protein level of MUC-1 | Increased |
| the protein level of any one or more lysosomal proteins | Increased |
| the protein level of one or more lysosomal proteases | Increased |
| the activity level of one or more NEU1 substrates | Increased |
| the activity level of LAMP-1 | Increased |
| the activity level of MUC-1 | Increased |
| The overall level of sialylation in a sample | Increased |
| the sialylation level of one or more NEU1 substrates | Increased |
| the sialylation level of LAMP-1 | Increased |
| the sialylation level of MUC-1 | Increased |
| the protein level of one or more cathepsins | Increased |
| the protein level of Hexosaminidase beta | Increased |
| the protein level of mannosidase alpha | Increased |
| Increased Sialylation Activity | |
| the level of NEU1 protein | Decreased |
| The level of NEU1 enzymatic activity | Decreased |
| the protein level of one or more NEU1 substrates | Increased |
| the protein level of LAMP-1 | Increased |
| the protein level of MUC-1 | Increased |
| the activity level of one or more NEU1 substrates | Increased |
| the activity level of LAMP-1 | Increased |
| the activity level of MUC-1 | Increased |
| the overall level of sialylation in a sample | Increased |
| the sialylation level of one or more NEU1 substrates | Increased |
| the sialylation level of LAMP-1 | Increased |
| the sialylation level of MUC-1 | Increased |
| Decreased Lysosomal Sialidase Activity | |
| the level of NEU1 protein | Decreased |
| the level of NEU1 enzymatic activity | Decreased |
| the protein level of one or more NEU1 substrates | Increased |
| the protein level of LAMP-1 | Increased |
| the protein level of MUC-1 | Increased |
| The activity level of one or more NEU1 substrates | Increased |
| the activity level of LAMP-1 | Increased |
| the activity level of MUC-1 | Increased |
| the sialylation level of one or more NEU1 substrates | Increased |
| the sialylation level of LAMP-1 | Increased |
| the sialylation level of MUC-1 | Increased |
| Increased NEU1 Substrate Sialylation Activity | |
| the sialylation level of one or more NEU1 substrates | Increased |
| the sialylation level of LAMP-1 | Increased |

TABLE 2-continued

Summary of alterations in various markers employed to establish an increase or decrease in a specific type of activity.

| Marker | Level of Marker Compared to Control |
|---|---|
| the sialylation level of MUC-1 | Increased |
| Increased NEU1 Level Activity | |
| the protein level of one or more non-MUC-1 NEU1 substrates | Increased |
| the protein level of MUC-1- only in combination with another NEU1 substrate | Increased |
| the protein level of LAMP-1 | Increased |
| the protein level of MUC-1 | Increased |

IV. Cancer

The various profiles provided herein can be used in methods of prognosis of a chemotherapy regime, diagnosis of cancer and prognosis of cancer in a subject. As provided herein "prognosis" is the likely outcome of a pathological condition or disease (i.e. the expected morbidity or mortality, the expected outcome of a therapy, or the risk of metastasis). "Diagnosis" refers to determining whether a subject is likely to have a disease or condition.

As mentioned in the previous section, NEU1 is a regulator of lysosomal exocytosis. Moreover, NEU1 is the only known regulator of lysosomal exocytosis. Defects in lysosomal exocytosis have been associated with various diseases. For example, NEU1 deficiency results in the lysosomal storage disease sialidosis.

Under conditions where NEU1 levels or enzyme activity are low, the NEU1 substrate, LAMP-1, accumulates in an over-sialylated state in the lysosome. As discussed, LAMP-1 enhances lysosomal exocytosis. As such, a lower lysosomal sialidase activity results in an increase in lysosomal exocytosis and release of lysosomal contents into the extracellular space.

Described herein is the discovery that cancer cells and tumors from various types of cancers have a low lysosomal sialidase activity (i.e. as measured using any of the lysosomal sialidase activity markers provided herein). See, for example, Example 1 described elsewhere herein. In such cases, the down-regulation of NEU1 leads to a deregulation of lysosomal exocytosis in the cancer cells, thus increasing lysosomal exocytosis.

Excessive lysosomal exocytosis can have profound effects on cancer diagnosis, prognosis and chemotherapy as discussed herein. The methods of determining the prognosis of a lysosomotropic chemotherapeutic agent, and the diagnosis and prognosis of cancer provided herein encompass any type of cancer in a subject. Non-limiting examples of types of cancer encompassed by the methods herein include, sarcomas, leukemia, lymphoma, breast cancer, colon cancer, rhabdomyosarcoma, Ewing's sarcoma, lung cancer, bladder cancer, pancreatic cancer, ovarian cancer, prostate cancer, brain tumors, acute lymphoblastic leukemia, and bone cancer. In specific embodiments, the cancer comprises rhabdomyosarcoma, breast cancer, colon cancer, pancreatic cancer or Ewing's sarcoma.

A. Methods of Prognosis of a Chemotherapy Regime

Provided herein are methods of determining the prognosis for a lysosomotropic chemotherapeutic agent regime in a subject with cancer. As used herein, a "lysosomotropic chemotherapeutic agent" is meant any chemotherapeutic agent that accumulates preferentially in the lysosomes of cells. Many commonly used chemotherapeutic agents accumulate in the acidic lysosome due to their weakly basic nature. Some non-limiting examples of lysosomotropic chemotherapeutic agents include doxorubicin, cisplatin and docetaxel.

In cases where NEU1 is down-regulated in a cancer, this leads to a deregulation of lysosomal exocytosis in the cancer cells, thus increasing lysosomal exocytosis. As such, chemotherapeutic agents which accumulate in the lysosomes are released from the cancer cells into the extracellular space thereby preventing the chemotherapy from having an effect on the cell. Thus, a low lysosomal sialidase activity is predictive of chemotherapy resistance to lysosomotropic chemotherapeutic agents. By "resistant" to chemotherapy is meant the ability of a cell or tumor to withstand the effects of a chemotherapeutic agent(s).

The prognosis for a lysosomotropic chemotherapeutic agent regime in a subject with cancer can be determined by obtaining a lysosomal sialidase activity profile of a sample from the subject with cancer. In such cases, an alteration in the lysosomal sialidase activity of any one or more lysosomal sialidase activity markers as compared to a control sample, as depicted, for example, in Table 2, results in a lower or decreased lysosomal sialidase activity for the sample. In the case where the lysosomal sialidase activity is lower in the subject sample as compared to a control sample, it is predicted that the cancer will be resistant to the lysosomotropic chemotherapy.

In one embodiment, the method of determining the prognosis for a lysosomotropic chemotherapeutic agent regime in a subject with cancer comprises the steps of: (a) providing a subject lysosomal sialidase activity profile from a tumor sample from the subject; (b) providing a reference lysosomal sialidase activity profile from a control sample, wherein the subject lysosomal sialidase activity profile and the reference lysosomal sialidase activity profile comprise one or more values representing lysosomal sialidase activity; and (c) comparing the subject and the reference lysosomal sialidase activity profiles to thereby determine the prognosis for a lysosomotropic chemotherapeutic agent regime in the subject, wherein a lower lysosomal sialidase activity of the subject as compared to the lysosomal sialidase activity of the reference results in a prediction that the cancer will be resistant to the lysosomotropic chemotherapeutic agent.

In one embodiment, the lysosomal sialidase activity profile comprises any number and combination of lysosomal sialidase activity values for any of the various lysosomal sialidase activity markers provided herein. Non-limiting examples of the lysosomal sialidase activity profile of a sample are provided in Table 1.

In a specific embodiment, the lysosomal sialidase activity comprises the level of LAMP-1 protein. In another embodiment, the lysosomal sialidase activity comprises the level of MUC-1 protein. In yet another embodiment, the lysosomal sialidase activity comprises the level of the NEU1 substrates LAMP-1 and MUC-1. In a further embodiment, the lysosomal sialidase activity comprises the level of LAMP-1 sialylation. In yet another embodiment, the lysosomal sialidase activity comprises the level of MUC-1 sialylation. In another specific embodiment, the level of lysosomal sialidase activity comprises the level of LAMP-1 and MUC-1 sialylation. In still further embodiments, the lysosomal sialidase activity comprises the level of LAMP-1, the level of MUC-1, the level of sialylation of LAMP-1 and the level of MUC-1 sialylation.

Knowledge of the lysosomal sialidase activity status of a tumor from a subject will allow the physician to predict the most appropriate therapy for a subject having a cancer with a low lysosomal sialidase activity profile. For example, lysosomotropic chemotherapeutic agents would not be chosen for treating a tumor with low lysosomal sialidase activity profile since this is predictive that the tumor will be resistant to these agents. Thus, a treatment regime with chemotherapeutic drugs that do not accumulate in the lysosome would be a better treatment option.

B. Methods of Diagnosis and Prognosis of Cancer

The methods herein also provide a method of determining the prognosis and diagnosis for a subject with cancer. Information obtained from the diagnosis and prognosis can be useful in selecting an appropriate treatment.

As described elsewhere herein, NEU1 is a negative regulator of lysosomal exocytosis and low lysosomal sialidase activity results in an increase in lysosomal exocytosis. Excess lysosomal exocytosis can have profound effects on the extracellular environment of a cell. For example, the lysosome contains proteases which breakdown the extracellular matrix resulting in a remodeling of the extracellular environment. The breakdown of the extracellular matrix increases the vulnerability of tissue to invasion. As such, a high concentration of proteases in the extracellular matrix surrounding a cancer cell can enhance the invasive potential and metastasis of a cancer cell.

A cancer that is "invasive" has the ability to spread to the surrounding tissue. "Metastasis", as used herein, refers to the process by which a cancer spreads or transfers from the site of origin to other regions of the body. As depicted elsewhere herein, cancers that have low lysosomal sialidase activity have an increased invasive potential. Assays that measure the invasiveness of a cancer are known in the art and an example invasion assay is described in detail in Example 1 provided elsewhere herein.

Invasive cancers are more likely to metastasize and thus have an unfavorable prognosis, whereas non-invasive cancers are less likely to metastasize and therefore have a favorable prognosis. The term "unfavorable prognosis" in regards to tumors or subjects diagnosed with cancer refers to a tumor or subject with a high probability of metastasis and/or a high probability of causing death or dying. A "favorable prognosis" in regards to a subject diagnosed with cancer refers to a tumor or subject with a low probability of metastasis and/or a low probability of causing death or dying.

The lysosomal sialidase activity of a sample, for the purpose of diagnosis and prognosis of cancer, can be determined by measuring the values for any two or more of the various lysosomal sialidase activity markers provided herein. Thus, lower levels of lysosomal sialidase activity in a subject sample as compared to a reference lysosomal sialidase activity of a control sample are indicative that a tumor has increased invasive potential (i.e. an unfavorable prognosis), while higher or normal levels of lysosomal sialidase activity in a subject sample as compared to a reference lysosomal sialidase activity of a control sample are predictive of a less invasive potential (i.e. a favorable prognosis).

In some embodiments the diagnosis and/or prognosis of cancer can be determined by measuring the NEU1 substrate sialylation activity or the NEU1 level activity of a sample. These activities can be determined by measuring the values for any of the various markers provided in Tables 1 and 2. For a NEU1 substrate sialylation activity, a higher level of any one or more NEU1 substrate sialylation activity markers results in a higher NEU1 substrate sialylation activity and is indicative of cancer and an unfavorable prognosis. For a NEU1 level activity, a higher level of any two or more NEU1 substrate activity markers results in a higher NEU1 level activity and is indicative of cancer and an unfavorable prognosis.

In one embodiment, a method of determining the prognosis for a subject with a cancer is provided and comprises the steps of: (a) providing a subject lysosomal sialidase activity profile comprising two or more values from different lysosomal sialidase activity markers, a NEU1 substrate sialylation activity profile or a NEU1 level activity profile from a tumor sample from the subject; (b) providing a corresponding reference lysosomal sialidase activity profile comprising two or more values from different lysosomal sialidase activity markers, a NEU1 substrate sialylation activity profile or a NEU1 level activity profile from a control sample, wherein the subject profile and the reference profile comprise one or more values representing lysosomal sialidase activity, NEU1 substrate sialylation activity or NEU1 level activity; and (c) comparing the subject and the reference lysosomal sialidase activity profiles, NEU1 substrate sialylation activity profiles or NEU1 level activity profiles to thereby determine the prognosis for the subject with cancer, wherein a lower lysosomal sialidase activity, a higher NEU1 substrate sialylation activity or a higher NEU1 level activity of the subject as compared to the lysosomal sialidase activity, NEU1 substrate sialylation activity or NEU1 level activity of the reference results in a prediction of an invasive cancer for the subject.

In another embodiment, a method of diagnosing cancer in a subject is provided, the method comprising: (a) providing a subject profile comprising a lysosomal sialidase activity profile comprising two or more values from different lysosomal sialidase activity markers, a NEU1 substrate sialylation activity profile or a NEU1 level activity profile from a tumor sample from the subject; (b) providing a corresponding reference profile comprising a lysosomal sialidase activity profile comprising two or more values from different lysosomal sialidase activity markers, a NEU1 substrate sialylation activity profile or a NEU1 level activity profile from a control sample, wherein the subject profile and the reference profile comprise one or more values representing lysosomal sialidase activity, NEU1 substrate sialylation activity or NEU1 level activity; and (c) comparing the subject and the reference lysosomal sialidase activity profiles, NEU1 substrate sialylation profiles or NEU1 level profiles to thereby determine the diagnosis for the subject, wherein the subject is diagnosed with cancer if the lysosomal sialidase activity of the subject is lower, the NEU1 substrate sialylation activity is higher or the NEU1 level activity is higher than the lysosomal sialidase activity, the NEU1 substrate sialidase activity or the NEU1 level activity of the reference.

Knowledge of the level of lysosomal sialidase activity, NEU1 substrate sialylation activity or NEU1 level activity in a subject sample allows a practitioner to diagnose a subject as having cancer, predict the aggressiveness of a cancer and thereby select the appropriate therapy for the subject with cancer.

V. Methods of Diagnosis of Dementia Associated with Alzheimer's Disease

Also provided herein are methods for the diagnosis of dementia associated with Alzheimer's disease. Provided herein, is a demonstration that the lysosomal exocytosis activity profile of a sample from a subject is predictive of dementia associated with Alzheimer's disease.

As used herein, "dementia associated with Alzheimer's disease" is characterized by the standard criteria for dementia as reported in the Recommendations from the National Institute on Aging-Alzheimer's Association workgroups on diagnostic guidelines for Alzheimer's disease. The standard criteria for dementia include (1) cognitive or behavioral symptoms that interfere with the ability to function at usual activities or work, denote a decline from previous functioning and performing levels and cannot be explained by a major psychiatric disorder or delirium; (2) detection and diagnosis of cognitive impairment through a combination of history-taking from the patient and a knowledgeable informant and an objective cognitive assessment; and (3) the cognitive or behavioral impairment involves two or more of the following: (a) impaired ability to acquire and remember new information; (b) impaired reasoning and handling of complex tasks, poor judgment; (c) impaired visuospatial abilities; (d) impaired language functions; and (e) changes in personality, behavior or comportment. Dementia associated with Alzheimer's can further have one or more of the following characteristics: (1) meets all criteria for dementia as described above; (2) insidious onset; (3) a history of worsening or cognition by report or observation; (4) amnestic presentation; and (5) nonamnestic presentations, such as, language presentation, visuospatial presentation or executive dysfunction. The Alzheimer's disease dementia guidelines are described in detail in McKhann et al. (2011) *Alzheimer's & Dementia* 7:263-69, herein incorporated by reference in its entirety.

As described elsewhere herein, NEU1 is a negative regulator of lysosomal exocytosis. In such instances when NEU1 protein levels or enzymatic activity are low, lysosomal exocytosis is enhanced. As shown herein, under conditions where the NEU1 protein level is low, highly sialylated proteins can be detected in the cerebrospinal fluid (CSF). In such cases, the composition of the CSF is changed and many of the highly sialylated proteins also have increased levels in the CSF. These proteins that are changed in the CSF under conditions of low NEU1 protein and activity levels correlate with biomarkers for predicting dementia associated with Alzheimer's disease. For example, amyloid precursor protein (APP) is shown herein to be a NEU1 substrate and accumulates in the brain and CSF in a highly sialylated form under low NEU1 conditions. Lysosomes also comprise proteases that can process APP to form toxic Aβ peptides. Thus, excessive lysosomal exocytosis (i.e. when NEU1 protein or enzymatic activity levels are low) enhances the plaque formation that is characteristic of Alzheimer's disease. See, for example, Example 3, provided elsewhere herein. Thus, in one embodiment, an increased lysosomal exocytosis activity, as described in detail elsewhere herein, in the CSF can be predictive of dementia associated with Alzheimer's disease.

A variety of proteins can have an increased sialylation level and/or have increased levels in the CSF. In some embodiments, the proteins having an increased sialylation level and/or protein level are NEU1 substrates. In other embodiments, the proteins having an increased sialylation level and/or protein level are lysosomal proteins. Non-limiting examples of proteins with increased sialylation and/or protein level include LAMP-1, MUC-1, Cathepsin B, Cathepsin D, Complement system proteins, Fibrinogen, Hexosaminidase beta, Mannosidase alpha, Transthyretin, beta-2 microglobulin and Amyloid Precursor Protein. Any one or more of these proteins can be a marker for lysosomal exocytosis activity.

Provided herein is a method of diagnosing dementia associated with Alzheimer's disease in a subject, the method comprising: (a) providing a subject lysosomal exocytosis activity profile of a sample of cerebrospinal fluid from the subject; (b) providing a reference lysosomal exocytosis activity profile of a control sample of cerebrospinal fluid, wherein the subject lysosomal exocytosis activity profile and the corresponding reference lysosomal exocytosis activity profile comprise one or more values representing lysosomal exocytosis activity; and (c) comparing the subject and the reference lysosomal exocytosis activity profiles, wherein the subject is diagnosed with dementia associated with Alzheimer's disease if the subject has a higher lysosomal exocytosis activity as compared to the reference lysosomal exocytosis activity.

In one embodiment the lysosomal exocytosis activity profile comprises a lysosomal sialidase activity profile. The lysosomal sialidase activity profile can comprise any combination of any of the various lysosomal sialidase activity markers provided herein. In such cases, a low lysosomal sialidase activity in a subject sample as compared to a reference lysosomal sialidase activity in a control sample results in a subject being diagnosed with dementia associated with Alzheimer's disease.

In another embodiment, the lysosomal exocytosis activity profile comprises a sialylation activity profile. The sialylation activity profile can comprise any combination of any of the various sialylation activity markers provided herein. In such cases, a high sialylation activity in a subject sample as compared to a reference sialylation activity in a control sample results in a subject being diagnosed with dementia associated with Alzheimer's disease.

For the diagnosis of dementia associated with Alzheimer's disease, the lysosomal exocytosis activity profiles, the lysosomal sialidase activity profiles or the sialylation activity profiles can comprise any one or more of the various markers provided herein (i.e. see Tables 1 and 2).

Knowledge of the sialylation activity profile of a subject sample will allow the physician to make a diagnosis of dementia associated with Alzheimer's disease in a subject. Thus, an early diagnosis can be made and the appropriate treatment options can be considered for the subject.

VI. Methods of Generating a Lysosomal Sialidase Activity Profile and an Lysosomal Exocytosis Activity Profile Methods of generating a lysosomal sialidase activity profile and/or a lysosomal exocytosis activity profile for a sample are also provided. As presented herein, the lysosomal sialidase activity profile of a sample can comprise one or more lysosomal sialidase activity markers representing lysosomal sialidase activity (i.e. any of the various markers of lysosomal sialidase activity provided herein, see Table 1). Also herein, the lysosomal exocytosis activity profile of a sample can comprise one or more lysosomal exocytosis activity markers representing lysosomal exocytosis activity (i.e. any or the various markers of lysosomal exocytosis activity provided herein, see Table 1).

In one embodiment, a method of generating a lysosomal sialidase activity profile comprises: (a) obtaining a sample from a tumor from a subject; and (b) assaying for the level of LAMP-1 protein or the level of LAMP-1 sialylation. In a further embodiment, the method comprises assaying for one or more additional lysosomal sialidase activity markers. In yet another embodiment of the method, the one or more additional lysosomal sialidase activity markers comprise a NEU1 substrate. Assays for measuring the various lysosomal sialidase activity markers are provided elsewhere herein.

In another embodiment, a method of generating a lysosomal exocytosis activity profile from cerebrospinal fluid comprises: (a) obtaining a sample of cerebrospinal fluid from a subject; and (b) assaying for lysosomal exocytosis activity. In a specific embodiment, assaying for lysosomal exocytosis activity comprises assaying for the level of LAMP-1 protein or the level of LAMP-1 sialylation.

In a non-limiting embodiment, assaying for lysosomal exocytosis activity comprises assaying for the level of one or more proteins comprising LAMP-1, MUC-1, amyloid precursor protein, Cathepsin B, Cathepsin D, Fibrinogen, Hexosaminidase beta, Mannosidase alpha, Transthyretin, beta-2 microglobulin or Immunoglobulin heavy chain.

VII. Methods of Treatment

Further provided are methods of treating a subject having a cancer or having dementia associated with Alzheimer's disease. By "treating" a subject with cancer or dementia associated with Alzheimer's disease is intended administration of a therapeutically effective amount of NEU1 or an active variant or fragment thereof, administration of a therapeutically effective amount of protective protein/cathepsin A (PPCA) or an active variant or fragment thereof or administration of a therapeutically effective amount of a combination of NEU1 and PPCA to a subject that has cancer or dementia associated with Alzheimer's disease, where the purpose is to cure, heal, alleviate, relieve, alter, remedy, ameliorate, improve, or affect the condition or the symptoms of the cancer or dementia associated with Alzheimer's disease.

Also provided herein are methods of preventing a cancer or dementia associated with Alzheimer's disease in a subject. By "preventing" a cancer or dementia associated with Alzheimer's disease in a subject is intended administration of a therapeutically effective amount of NEU1 or an active variant or fragment thereof, administration of a therapeutically effective amount of protective protein/cathepsin A (PPCA) or an active variant or fragment thereof or administration of a therapeutically effective amount of a combination of NEU1 and PPCA to a subject, where the purpose is to protect the subject from development of a cancer or dementia associated with Alzheimer's disease. In some embodiments, a therapeutically effective amount of NEU1 or an active variant or fragment thereof, protective protein/cathepsin A (PPCA) or an active variant or fragment thereof or a combination of NEU1 and PPCA is administered to a subject, such as a human, that is at risk for developing a cancer or dementia associated with Alzheimer's disease.

A "therapeutically effective amount" as used herein refers to that amount which provides a therapeutic effect for a given condition and administration regimen. Thus, the phrase "therapeutically effective amount" is used herein to mean an amount sufficient to cause an improvement in a clinically significant condition in the host. In particular aspects, a "therapeutically effective amount" refers to an amount of NEU1, PPCA, or a combination of NEU1 and PPCA provided herein that when administered to a subject brings about a positive therapeutic response with respect to the treatment of a subject for a cancer or dementia associated with Alzheimer's disease. A positive therapeutic response in regard to treating a cancer includes curing or ameliorating the symptoms of the disease. In the present context, a deficit in the response of the host can be evidenced by continuing or spreading of the cancer. An improvement in a clinically significant condition in the host includes a decrease in the size of a tumor, increased necrosis of a tumor, clearance of the tumor from the host tissue, reduction or amelioration of metastasis, or a reduction in any symptom associated with the cancer. A positive therapeutic response in regard to treating a subject with dementia associated with Alzheimer's disease includes curing or ameliorating the symptoms of the disease. In this context, a deficit in the response of the host can be evidenced by continuing or worsening of the dementia associated with Alzheimer's disease. An improvement in a clinically significant condition in the host includes a decrease in dementia (i.e. an improvement in memory, judgment, visuospatial abilities, language functions, behavior or any of the other symptoms of dementia provided elsewhere herein) in the subject.

In particular aspects, a "therapeutically effective amount" refers to an amount of NEU1, PPCA, or a combination of NEU1 and PPCA provided herein that when administered to a subject brings about a positive therapeutic response with respect to the prevention of a cancer or dementia associated with Alzheimer's disease in a subject. A positive therapeutic response with respect to preventing a cancer or dementia associated with Alzheimer's disease in a subject, for example, is the prevention of development of the disease in a subject.

In one embodiment, a method of treating a subject having a cancer comprises administering to a subject in need thereof a therapeutically effective amount of Neuraminidase 1 (NEU1) having an amino acid sequence with at least 85% sequence identity to SEQ ID NO: 2 or an active variant or fragment thereof.

In another embodiment, a method of treating a subject with dementia associated with Alzheimer's disease comprises administering to a subject in need thereof a therapeutically effective amount of Neuraminidase 1 (NEU1) having an amino acid sequence with at least 85% sequence identity to SEQ ID NO: 2 or an active variant or fragment thereof.

In some embodiments, the methods can further comprise administration of Protective Protein/Cathepsin A (PPCA) having an amino acid sequence with at least 85% sequence identity to SEQ ID NO: 4.

In other embodiments, the administration of NEU1 and PPCA can be separate or NEU1 and PPCA can be administered to a subject simultaneously. The administration can be by any known method of administration as described elsewhere herein. In one embodiment, the administration of NEU1 and/or PPCA comprises administration of a viral vector comprising a nucleotide sequence having at least 85% sequence identity to SEQ ID NO: 1 and/or a nucleotide sequence having at least 85% sequence identity to SEQ ID NO: 3.

Active variants and fragments of NEU1 can be used in the methods provided herein. Such active variants can comprise at least 65%, 70%, 75%, 80%, 85%, 90%, 91%, 92%, 93%, 94%, 95%, 96%, 97%, 98%, 99% or more sequence identity to SEQ ID NO: 2, wherein the active variants retain biological activity and hence have sialidase activity. Sialidase activity is described in detail elsewhere herein. Active variants of NEU1 are known in the art. There are over 130 types of neuraminidases known from various species ranging from viruses to humans. See, for example, Monti et al. (2010) *Adv. Carbohydr. Chem. Biochem.* 64:403-79, herein incorporated by reference in its entirety.

Active variants and fragments of PPCA can be used in the methods provided herein. Such active variants can comprise at least 65%, 70%, 75%, 80%, 85%, 90%, 91%, 92%, 93%, 94%, 95%, 96%, 97%, 98%, 99% or more sequence identity to SEQ ID NO:4, wherein the active variants retain biological activity and hence enhances NEU1 enzymatic activity. Assays to measure for NEU1 enzymatic activity are described elsewhere herein. Active variants of PPCA are known in the art. See, for example, Galjart et al. (1988) *Cell* 54(6):755-64, herein incorporated by reference in its entirety.

VIII. Methods of Administration

The methods of treatment for cancer and dementia associated with Alzheimer's disease provided herein can encompass administration of treatment via any parenteral route, including, but not limited to, intramuscular, intraperitoneal, intravenous, and the like.

Further, as used herein "pharmaceutically acceptable carriers" are well known to those skilled in the art and include, but are not limited to, 0.01-0.1 M, or 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also comprehended herein are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions presented herein incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may therefore elicit relatively short-lived pharmacological activity. Consequently, frequent administrations of relatively large doses of bioactive compounds may be required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages. The sufficient amount may include but is not limited to from about 1 µg/kg to about 100 mg/kg, from about 100 µg/kg to about 1 mg/kg, from about 1 mg/kg to about 10 mg/kg, about 10 mg/kg to about 100 mg/kg, from about 100 mg/kg to about 500 mg/kg or from about 500 mg/kg to about 1000 mg/kg. The amount may be 10 mg/kg. The pharmaceutically acceptable form of the composition includes a pharmaceutically acceptable carrier.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The component or components of a therapeutic composition provided herein may be introduced parenterally, transmucosally, e.g., orally, nasally, pulmonarily, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. The term "unit dose" when used in reference to a therapeutic composition provided herein refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer (1990) Science 249:1527-1533; Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In yet another embodiment, the therapeutic compound can be delivered in a controlled release system. For example, the protein may be administered using intravenous infusion, an implantable osmotic pump, a transdermal patch, liposomes, or other modes of administration. In one embodiment, a pump may be used (see Langer, supra; Sefton (1987) *CRC Crit. Ref Biomed. Eng.* 14:201; Buchwald et al. (1980) *Surgery* 88:507; Saudek et al. (1989) *N. Engl. J. Med.* 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas (1983) *J. Macromol. Sci. Rev. Macromol. Chem.* 23:61; see also Levy et al. (1985) *Science* 228:190; During et al. (1989) *Ann. Neurol.* 25:351; Howard et al. (1989) *J. Neurosurg.* 71:105). In yet another embodiment, a controlled release system can be placed in proximity of the therapeutic target, i.e., the brain or a tumor, thus requiring only a fraction of the systemic dose (see, e.g., Goodson, in *Medical Applications of Controlled Release*, supra, vol. 2, pp. 115-138 (1984)). Other controlled release systems are discussed in the review by Langer (1990) *Science* 249:1527-1533.

A subject in whom administration of an active component as set forth above is an effective therapeutic regimen for a cancer or dementia associated with Alzheimer's disease is preferably a human, but can be any animal. Thus, as can be readily appreciated by one of ordinary skill in the art, the methods and pharmaceutical compositions provided herein are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions provided herein, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with other compounds. For treatment of cancer or dementia associated with Alzheimer's disease, one may administer the present active component in conjunction with one or more pharmaceutical compositions used for treating cancer or dementia associated with Alzheimer's disease, including but not limited to (1) chemotherapeutic agents; or (2) other drugs for treating symptoms of Alzheimer's including domepezil, galantamine, memantine, rivastigmine or tacrine. Administration may be simultaneous (for example, administration of a mixture of the present active component and a chemotherapeutic agent), or may be in seriatim.

Also contemplated are dry powder formulations comprising at least one protein provided herein and another therapeutically effective drug, such as a chemotherapeutic agent or a drug for treating Alzheimer's disease.

Contemplated for use herein are oral solid dosage forms, which are described generally in Remington's Pharmaceutical Sciences, 18th Ed.1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013, 556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where the moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis (1981) "Soluble Polymer-Enzyme Abducts" In: *Enzymes as Drugs*, Hocenberg and Roberts, eds., Wiley-Interscience, New York, N.Y., pp. 367-383; Newmark, et al. (1982) *J. Appl. Biochem.* 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), EUDRAGIT L30D coating, AQUATERIC coating, cellulose acetate phthalate (CAP), EUDRAGIT L coating, EUDRAGIT S coating, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The peptide therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextran and starch. Certain inorganic salts may be also used as fillers including calcium triphosphate, magnesium carbonate and sodium chloride. Some commercially available diluents are FAST-FLO diluent, EMDEX diluent, STA-RX 1500 diluent, EMCOMPRESS diluent and AVICEL diluent.

Disintegrants may be included in the formulation of the therapeutic into a solid dosage form. Materials used as disintegrates include but are not limited to starch, including the commercial disintegrant based on starch, EXPLOTAB disintegrant. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, CARBOWAX4000 lubricant, and CARBOWAX 6000 lubricant.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the protein (or derivative) are for instance the fatty acids oleic acid, linoleic acid and linolenic acid.

In one embodiment, the method comprises the use of viruses for administering NEU1 and/or PPCA to a subject. Administration can be by the use of viruses that express NEU1 and/or PPCA, such as recombinant retroviruses, recombinant adeno-associated viruses, recombinant adenoviruses, and recombinant Herpes simplex viruses (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)).

A NEU1 and/or PPCA gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.* 193: 653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad. Sci. USA* 86:317 (1989), and Flexner et al., *Ann. N.Y. Acad. Sci.* 569:86 (1989)), and retroviruses (e.g., Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399, 346). Within various embodiments, either the viral vector itself, or a viral particle, which contains the viral vector may be utilized in the methods described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant herpes simplex virus can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), *HSV Virus Protocols* (Humana Press 1997).

When the subject treated with a recombinant virus is a human, then the therapy is preferably somatic cell gene therapy. That is, the preferred treatment of a human with a recombinant virus does not entail introducing into cells a nucleic acid molecule that can form part of a human germ line and be passed onto successive generations (i.e., human germ line gene therapy).

IX. Variants and Fragments

Fragments and variants of the polynucleotides encoding the NEU1 and PPCA polypeptides can be employed in the various methods and compositions of the invention. By "fragment" is intended a portion of the polynucleotide and hence the protein encoded thereby or a portion of the polypeptide. Fragments of a polynucleotide may encode protein fragments that retain the biological activity of the native protein. Thus, fragments of a polynucleotide may range from at least about 20 nucleotides, about 50 nucleotides, about 100 nucleotides, about 150, about 200, about 250, about 300, about 350, about 400, about 450, about 500, about 550, about 600 and up to the full-length polynucleotide encoding the NEU1 or PPCA polypeptide.

A fragment of a polynucleotide that encodes a biologically active portion of a NEU1 or PPCA polypeptide will encode at least 15, 25, 30, 50, 100, 150, 200, or 250 contiguous amino acids, or up to the total number of amino acids present in a full-length NEU1 or PPCA polypeptide.

A biologically active portion of a NEU1 or PPCA polypeptide can be prepared by isolating a portion of one of the polynucleotides encoding the portion of the NEU1 or PPCA polypeptide and expressing the encoded portion of the polypeptide (e.g., by recombinant expression in vitro), and assessing the activity of the portion of the NEU1 or PPCA polypeptide. Polynucleotides that encode fragments of a NEU1 or PPCA polypeptide can comprise nucleotide sequence comprising at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length NEU1 or PPCA nucleotide sequence disclosed herein.

"Variant" sequences have a high degree of sequence similarity. For polynucleotides, conservative variants include those sequences that, because of the degeneracy of the genetic code, encode the amino acid sequence of one of the NEU1 or PPCA polypeptides. Variants such as these can be identified with the use of well-known molecular biology techniques, as, for example, polymerase chain reaction (PCR) and hybridization techniques. Variant polynucleotides also include synthetically derived nucleotide sequences, such as those generated, for example, by using site-directed mutagenesis but which still encode a NEU1 or PPCA polypeptide. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the NEU1 or PPCA polypeptides set forth herein. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins are biologically active, that is they continue to possess the desired biological activity of the native protein. Such variants may result from, for example, genetic polymorphism or from human manipulation. Biologically active variants of a NEU1 or PPCA polypeptides will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein may differ from that protein by as few as 1-15 amino acid residues, as few as 1-10, such as 6-10, as few as 5, as few as 4, 3, 2, or even 1 amino acid residue.

Proteins may be altered in various ways including amino acid substitutions, deletions, truncations, and insertions. Methods for such manipulations are generally known in the art. For example, amino acid sequence variants of the NEU1 or PPCA proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the polynucleotides used in the invention can include the naturally occurring sequences, the "native" sequences, as well as mutant forms. Likewise, the proteins used in the methods of the invention encompass naturally occurring proteins as well as variations and modified forms thereof. Such variants will continue to possess the ability to implement a recombination event. Generally, the mutations made in the polynucleotide encoding the variant polypeptide should not place the sequence out of reading frame, and/or create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant polynucleotides and proteins also encompass sequences and proteins derived from a mutagenic and recombinogenic procedure such as DNA shuffling. With such a procedure, one or more different NEU1 or PPCA coding sequences can be manipulated to create new NEU1 or PPCA polypeptides possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

X. Sequence Identity

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

As used herein, the singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

The subject matter of the present disclosure is further illustrated by the following non-limiting examples.

TABLE 3

Summary of SEQ ID NOS.

| SEQ ID NO | NA/AA | Description |
|---|---|---|
| 1 | NA | Neuraminidase 1 nucleic acid sequence. |
| 2 | AA | Neuraminidase 1 amino acid sequence. |
| 3 | NA | PPCA nucleic acid sequence. |
| 4 | AA | PPCA amino acid sequence. |

Non-limiting examples of methods disclosed herein are as follows:

1. A method of determining the prognosis for a subject with cancer, comprising the steps of a) providing a subject profile comprising a lysosomal sialidase activity profile comprising two or more values from different lysosomal sialidase activity markers, a NEU1 substrate sialylation activity profile or a NEU1 level activity profile from a tumor sample from said subject;

b) providing a corresponding reference profile comprising a lysosomal sialidase activity profile comprising two or more values from different lysosomal sialidase activity markers, a NEU1 substrate sialylation activity profile or a NEU1 level activity profile from a control sample, wherein the subject profile and the reference profile comprise one or more values representing lysosomal sialidase activity, NEU1 substrate sialylation activity or NEU1 level activity; and c) comparing said subject and said reference lysosomal sialidase activity profiles to thereby determine the prognosis for said subject with cancer, wherein a lower lysosomal sialidase activity, a higher NEU1 substrate sialylation activity or a higher NEU1 level activity of said subject as compared to the lysosomal sialidase activity, NEU1 substrate sialylation activity or NEU1 level activity of said reference results in a prediction of an invasive cancer for said subject.

2. A method of diagnosing cancer in a subject, the method comprising:

a) providing a subject profile comprising a lysosomal sialidase activity profile comprising two or more values from different lysosomal sialidase activity markers, a NEU1 substrate sialylation activity profile or a NEU1 level activity profile from a tumor sample from said subject;

b) providing a corresponding reference profile comprising a NEU1 activity profile comprising two or more values from different lysosomal sialidase activity markers, a NEU1 substrate sialylation activity profile or a NEU1 level activity profile from a control sample, wherein the subject profile and the reference profile comprise one or more values representing lysosomal sialidase activity, NEU1 substrate sialylation activity or NEU1 level activity; and c) comparing said subject and said reference lysosomal sialidase activity profiles to thereby determine the diagnosis for said subject, wherein said subject is diagnosed with cancer if said lysosomal sialidase activity of said subject is lower, the NEU1 substrate sialylation activity is higher or the NEU1 level activity is higher than the lysosomal sialidase activity, NEU1 substrate sialylation activity or NEU1 level activity of said reference.

3. A method of determining the prognosis for a lysosomotropic chemotherapeutic agent regime in a subject with cancer, comprising the steps of a) providing a subject lysosomal sialidase activity profile from a tumor sample from said subject;

b) providing a reference lysosomal sialidase activity profile from a control sample, wherein the subject lysosomal sialidase activity profile and the reference lysosomal sialidase activity profile comprise one or more values representing lysosomal sialidase activity; and c) comparing said subject and said reference lysosomal sialidase activity profiles to thereby determine the prognosis for a lysosomotropic chemotherapy agent regime in the subject, wherein a lower lysosomal sialidase activity of said subject as compared to the lysosomal sialidase activity of said reference results in a prediction that said cancer will be resistant to said lysosomotropic chemotherapeutic agent.

4. The method of any one of embodiments 1, 2 or 3, wherein the control sample is from normal tissue adjacent to said tumor from said subject.

5. The method of any one of embodiments 1, 2 or 3, wherein the one or more values representing lysosomal sialidase activity comprise the level of LAMP-1 protein.

6. The method of any one of embodiments 1, 2 or 3, wherein the one or more values representing lysosomal sialidase activity comprise the level of LAMP-1 and MUC-1 protein.

7. The method of any one of embodiments 1, 2 or 3, wherein the one or more values representing lysosomal sialidase activity comprise the level of LAMP-1 sialylation.

8. The method of any one of embodiments 1, 2 or 3, wherein the one or more values representing lysosomal sialidase activity comprise the level of MUC-1 sialylation.

9. The method of any one of embodiments 1, 2 or 3, wherein the one or more values representing lysosomal sialidase activity comprise the level of LAMP-1 and MUC-1 sialylation.

10. The method of any one of embodiments 1, 2 or 3, wherein the one or more values representing lysosomal sialidase activity comprise the level of LAMP-1, the level of MUC-1 protein, the level of LAMP-1 sialylation and the level of MUC-1 sialylation.

11. The method of embodiment 1, wherein the one or more values representing lysosomal sialidase activity comprise the level of MUC-1 protein.

12. The method of any one of embodiments 1-11, wherein the cancer comprises rhabdomyosarcoma, breast cancer, colon cancer, pancreatic cancer, acute lymphoblastic leukemia or Ewing's sarcoma.

13. A method of diagnosing dementia associated with Alzheimer's disease in a subject, the method comprising:

a) providing a subject lysosomal exocytosis activity profile of a sample of cerebrospinal fluid from said subject;

b) providing a reference lysosomal exocytosis activity profile of a control sample of cerebrospinal fluid, wherein the subject lysosomal exocytosis activity profile and the corresponding reference lysosomal exocytosis activity profile comprise one or more values representing lysosomal exocytosis activity; and, c) comparing said subject and said reference lysosomal exocytosis activity profiles, wherein said subject is diagnosed with dementia associated with Alzheimer's disease if the subject has a higher lysosomal exocytosis activity as compared to the reference lysosomal exocytosis activity.

14. The method of embodiment 13, wherein said subject lysosomal exocytosis activity profile and said reference lysosomal exocytosis activity profile comprise (a) a lysosomal sialidase activity profile, wherein the subject lysosomal sialidase activity profile and the corresponding reference lysosomal sialidase activity profile comprise one or more values representing lysosomal sialidase activity; or (b) a sialylation activity profile, wherein the subject sialylation activity profile and the corresponding reference sialylation activity profile comprise one or more values representing sialylation activity.

15. The method of embodiment 13, wherein the one or more values representing lysosomal exocytosis activity comprise the level of LAMP-1 sialylation.

16. The method of embodiment 13, wherein the one or more values representing lysosomal exocytosis activity comprise the level of MUC-1 sialylation.

17. The method of embodiment 13, wherein the one or more values representing lysosomal exocytosis activity comprise the level of LAMP-1 and MUC-1 sialylation.

18. The method of embodiment 13, wherein the one or more values representing lysosomal exocytosis activity comprise the level of amyloid precursor protein sialylation.

19. The method of embodiment 13, wherein the one or more values representing lysosomal exocytosis activity comprises the level of sialylation of one or more proteins comprising LAMP-1, MUC-1, amyloid precursor protein, Cathepsin B, Cathepsin D, Fibrinogen, Transthyretin, beta-2 microglobulin or Immunoglobulin heavy chain.

20. The method of embodiment 13, wherein the one or more values representing lysosomal exocytosis activity comprise the level of LAMP-1 protein.

21. The method of embodiment 13, wherein the one or more values representing lysosomal exocytosis activity comprise the level of MUC-1 protein.

22. The method of embodiment 13, wherein the one or more values representing lysosomal exocytosis activity comprise the level of amyloid precursor protein.
23. The method of embodiment 13, wherein the one or more values representing lysosomal exocytosis activity comprise the level of LAMP-1 and MUC-1 protein.
24. The method of embodiment 13, wherein the one or more values representing lysosomal exocytosis activity comprise the level of LAMP-1 protein, the level of MUC-1 protein, the level of LAMP-1 sialylation and the level of MUC-1 sialylation.
25. The method of embodiment 13, wherein the one or more values representing lysosomal exocytosis activity comprises the level of protein of one or more proteins comprising LAMP-1, MUC-1, amyloid precursor protein, Cathepsin B, Cathepsin D, Fibrinogen, Hexosaminidase beta, Mannosidase alpha, Transthyretin, beta-2 microglobulin or Immunoglobulin heavy chain.
26. A method of treating a subject having a cancer comprising administering to a subject in need thereof a therapeutically effective amount of Neuraminidase 1 (NEU1) polypeptide having an amino acid sequence with at least 85% sequence identity to SEQ ID NO: 2, wherein said polypeptide has sialidase activity.
27. A method of treating a subject with dementia associated with Alzheimer's disease comprising administering to a subject in need thereof a therapeutically effective amount of Neuraminidase 1 (NEU1) polypeptide having an amino acid sequence with at least 85% sequence identity to SEQ ID NO: 2, wherein said polypeptide has sialidase activity.
28. The method of any one of embodiments 26 or 27, further comprising the administration of Protective Protein/Cathepsin A (PPCA) polypeptide having an amino acid sequence with at least 85% sequence identity to SEQ ID NO: 4, wherein said PPCA polypeptide enhances NEU1 enzymatic activity.
29. The method of embodiment 28, wherein the NEU1 polypeptide and PPCA polypeptide are administered separately or simultaneously.
30. The method of embodiment 29, wherein administration of the NEU1 polypeptide comprises administration of a viral vector comprising a nucleotide sequence having at least 85% sequence identity to SEQ ID NO: 1.
31. A method of generating a lysosomal sialidase activity profile comprising:
    (a) obtaining a sample from a tumor from a subject; and,
    (b) assaying for the level of LAMP-1 protein or the level of LAMP-1 sialylation.
32. The method of embodiment 31, comprising assaying for one or more additional lysosomal sialidase activity markers.
33. The method of embodiment 32, wherein the one or more additional lysosomal sialidase activity markers comprise a NEU1 substrate.
34. A method of generating a lysosomal exocytosis activity profile from cerebrospinal fluid comprising:
    (a) obtaining a sample of cerebrospinal fluid from a subject; and,
    (b) assaying for lysosomal exocytosis activity.
35. The method of embodiment 34, wherein assaying for lysosomal exocytosis activity comprises assaying for the level of LAMP-1 protein or the level of LAMP-1 sialylation.
36. The method of embodiment 34, wherein assaying for lysosomal exocytosis activity comprises assaying for the level of one or more proteins comprising LAMP-1, MUC-1, amyloid precursor protein, Cathepsin B, Cathepsin D, Fibrinogen, Hexosaminidase beta, Mannosidase alpha, Transthyretin, beta-2 microglobulin or Immunoglobulin heavy chain.
37. The method of any one of embodiments 31-33, comprising assembling a lysosomal sialidase activity profile in view of the activity values obtained.
38. The method of any one of embodiments 34-36, comprising assembling a lysosomal exocytosis activity profile in view of the activity values obtained.
39. The method of any one of embodiments 1-38, wherein the subject is a human.

The subject matter of the present disclosure is further illustrated by the following non-limiting examples.

EXPERIMENTAL

Overview

We have discovered a novel association between lysosomal sialidase NEU1-regulated lysosomal exocytosis and two pathological states: (1) cancer and (2) Alzheimer's disease. The loss of NEU1 results in accumulation of its substrate LAMP-1, which, in turn, facilitates the exocytosis of lysosomal contents. The physiological consequences of this depend on the affected tissue. For instance, release of active proteases into the extracellular environment may cause remodeling of tissue surrounding a tumor. In the brain, this release may result in processing of amyloidogenic proteins and formation of plaques. In addition, xenobiotics, which accumulate in the lysosome may undergo efflux through this mechanism, altering drug metabolism. This application is of particular importance as a possible predictor of chemotherapy resistance in cancer cells and as prognostic marker of dementia related to Alzheimer's disease.

We have identified two read-outs for the loss of NEU1 which may be used to visualize NEU1 deficiency. These are substrates of NEU1, mucins and the aforementioned LAMP-1. We suggest that this is actually a possible proxy marker for NEU1 deficiency/downregulation and, therefore, increased lysosomal exocytosis. Thus, this marker, when combined with other NEU1 substrates, could be indicative of deregulated lysosomal exocytosis of cancer, which predicts both invasiveness and chemotherapy resistance.

Measuring NEU1 expression or catalytic activity in a cancer biopsy may have two somewhat related prognostic applications: 1) determine the state of the cancer: higher NEU1 activity=less aggressive/better prognosis; lower NEU1 activity=more aggressive/poorer prognosis; and 2) predict responsiveness to chemotherapy: higher NEU1 activity=less lysosomal exocytosis/less drug efflux extracellularly/more responsive; lower NEU1 activity=increased lysosomal exocytosis/more drug efflux/less responsive.

Alternatively, this information can be gleaned via a panel of NEU1 substrates. Accumulation of substrate glycoproteins in their oversialylated state as well as of active lysosomal enzymes indicate a global change in processing rather than a discrete upregulation in expression, which is currently assumed. This global change could then predict outcomes and could be used as fingerprint of invasive-low NEU1 tumors This discovery also has therapeutic application. By restoring the negative regulation of lysosomal exocytosis, cancer cells can become more treatable with chemotherapeutic drugs and less aggressive at the same time. This may be possible by administering NEU1 itself or by administering its stabilizing partner, protective protein/cathepsin A (PPCA), or by other means, i.e. LAMP1 downregulation.

Likewise, the downstream effects of lysosomal exocytosis can be used as a molecular fingerprint for Alzheimer's pathology. For instance, high levels of active lysosomal enzymes and other potential substrates of NEU1 in cerebral spinal fluid allow diagnosis of dementia related to late onset Alzheimer's disease in patients, filling a gap in patient care which currently exists.

This is a new approach for distinguishing more aggressive from less aggressive cancers that can help guide therapeutic decision-making. This invention also can lead to new cancer treatments and neurodegeneration therapies that may complement existing techniques or provide completely novel approaches.

Example 1: NEU1 Deficiency in Cancer Development, Progression, and Chemotherapy Resistance Deficiency of the lysosomal sialidase NEU1 results in the lysosomal storage disease sialidosis. Type I sialidosis is a catastrophic pediatric disease while Type II, or adult onset sialidosis, is a relatively mild condition caused by gene mutations which preserve residual activity of NEU1. Our own research into NEU1 deficiency, performed in the mouse model of sialidosis, has revealed a novel function of NEU1 as an inhibitor of lysosomal exocytosis. In the absence of NEU1, its substrate LAMP-1 accumulates, increasing the number of lysosomes docked at the PM and ready to engage in lysosomal exocytosis. As a result, lysosomal contents, including active proteases such as cathepsins, are aberrantly released extracellularly, most likely impacting the extracellular matrix structure and composition. We hypothesized that this phenotype could be advantageous for cancer cells, which extensively modify their extracellular matrix. We have therefore examined the expression of NEU1 in a variety of cancer cell lines from four cancer types: breast carcinoma, colon carcinoma, Ewing's sarcoma, and alveolar rhabdomyosarcoma. For each type of cancer examined, lower levels of NEU1 activity correlated with increased expression of over-sialylated LAMP-1. Here we report on a correlation between a low-NEU1, highly exocytic phenotype and the invasive capacity of cells. In some cases, the invasiveness of tested cell lines was known. For instance, the syngeneic system of SW480 and SW620 colon cancer lines is composed of cells derived from a primary or metastatic tumor, respectively, from the same patient. In other cases, such as for Ewings sarcoma and rhabdomyosarcoma, invasive potential of the tested cell lines was determined in our hands using an ex vivo model of peritoneal invasion. These studies establish a new paradigm for understanding the spread of cancer: invasive potential is enhanced by degradation of extracellular matrix via lysosomal exocytosis of active proteases.

Lysosomal exocytosis is part of constitutive cellular physiology which has particular importance for cancer cells. Translocation of lysosomal contents to the extracellular matrix (ECM) results in ECM remodeling and increased vulnerability of healthy tissue to invasion. In addition, many commonly used chemotherapeutics accumulate in the acidic lysosome due to their weakly basic nature. Lysosomal exocytosis therefore constitutes a method of xenobiotic efflux, relieving cancer cells of toxic burden. We have characterized the lysosomal enzyme Neuraminidase 1 as a negative regulator of lysosome exocytosis and here demonstrate the downregulation of NEU1 in several cancer types as well as the advantageous physiological consequences for cancer cells associated with the loss of NEU1.

In addition to its canonical role as a sialidase, NEU1 has a related and profound effect on the constitutive process of lysosomal exocytosis. This functionality is mediated by the NEU1 substrate Lysosomal Associated Membrane Protein 1 (LAMP1) which is left hyper-glycosylated in the absence of NEU1. This hyper-glycosylated state of LAMP1 appears to facilitate lysosomal docking at the plasma membrane (PM) and subsequent exocytosis causing a range of significant physiological changes to both the affected cell and its environment. Here we present data to demonstrate that loss of NEU1 and exacerbation of LEX result in two major physiological shifts in cancer cells: enhanced invasive potential and increased resistance to chemotherapy.

To first establish a general role for NEU1 in human cancer, we probed multiple tumor arrays for both NEU1 and two of its natural substrates, LAMP-1 and mucins. We found that downregulation of NEU1 in tumors compared to healthy tissue was occurred across cancer types and that using either LAMP-1 or mucin staining functioned as proxy markers for this change (data not shown). The finding is significant in part because the mucin MUC-1 has long been used as a trusted cancer marker and this research suggests that it may be downstream of another change with many other predictable, functional consequences.

In order to test functional consequences of changes to NEU1 levels in cancer, we evaluated several cell line systems (data not shown). In each, we assessed the NEU1 activity in lysates and the corresponding abundance of over-decorated LAMP-1. For each set evaluated, the relative invasive potential was determined either from literature or from matrigel invasion assays. The more invasive cells consistently demonstrated reduced NEU1 activity and increased LAMP1 levels compared to less invasive cells of the same cancer type (data not shown). We chose the RH41 and RH30 cell lines for further study because these alveolar rhabdomyosarcoma lines arise from skeletal muscle, a long-standing interest of our lab. The relatively high levels of NEU1 in RH41 cells compared to RH30 cells were further confirmed by archived microarray data, real time PCR, Western blot, and immunofluorescence. In addition to reduced LAMP-1 in RH41 cells, the high level of NEU1 correlates with a reduction of lysosomal exocytosis as measured by media activity assay and TIRF imaging (data not shown). To test the importance of NEU1 expression on these physiological markers, we generated stable clones of each line, with upregulation of NEU1 in RH30 cells and downregulation in RH41 cells, along with empty vector controls for each. Once the expression level of each line was recapitulated in the other, we tested for exocytosis changes via LAMP-1 and TIRF imaging (as well as activity assays). As predicted, we robustly demonstrated that NEU1 is a negative regulator of lysosomal exocytosis in the cancer cell context, marked by an accumulation of LAMP-1 (data not shown).

There are several immediate implications for identifying a regulator of lysosomal exocytosis in cancer cells. This process has been shown to contribute to both invasive potential and chemotherapy resistance, although a specific target for altering this process has not been proposed until NEU1. Lysosomal exocytosis is the most likely method for the efflux of active lysosomal enzymes into the extracellular matrix, and the presence of enzymes such as cathepsin B in the ECM correlates with metastasis across cancer types. Active proteases participate in ECM remodeling and inhibit the microenvironment's ability to contain tumor spread. Therefore, we tested the stable lines for their ability to invade a matrigel substrate, primarily composed of laminin and collagen IV, both susceptible to digestion by lysosomal enzymes such as cathepsins.

The stable clone lines for RH41 and RH30 were each plated onto matrigel plugs for two days. The plugs were then fixed, embedded, sectioned, and stained with H&E to visualize the ingress of cells into the substrate (data not shown). Regardless of parental line, those clones with low NEU1 successfully invaded the matrigel after two days whereas those cells with high NEU1 were excluded from the gel. This experiment established that the NEU1 status of cancer cells can determine the potential of cells to invade ECM.

However, we further wished to examine the longer term impact of lysosomal exocytosis on non-malignant tissue. We hypothesized that at a tumor border, excessive lysosomal exocytosis from the cancer would condition surrounding tissue for invasion, making healthy tissue more vulnerable to a metastatic event. We therefore tested the ability of the parental RH30 and RH41 cells to invade in an ex-vivo setting using peritoneum harvested from wild-type or Neu1-knockout mice. Tissues collected from Neu1 knockout mice have undergone constitutive excessive lysosomal exocytosis and can therefore represent the healthy tissue at the border of cancer undergoing excessive lysosomal exocytosis due to NEU1 downregulation. In fact, a the more invasive RH30 cells were able to cross into the peritoneum of wild type animals while the RH41 cells were largely excluded, recapitulating the results from the matrigel assay. Importantly, the less invasive RH41 cells were able to invade the knock out peritoneum as successfully as RH30 cells invaded the wild type. This result suggests that the damage done by long term lysosomal exocytosis sensitizes tissue to invasion, independent of the aggressiveness of the cancer. Furthermore, RH30 cells placed on knockout peritoneum resulted in the most aggressive rates on invasion. Therefore, we conclude that lysosomal exocytosis does significant damage to ECM, regardless of the source of the exocytosis. In the case of cancer cells, those with higher rates of exocytosis more successfully invade a standard substrate.

The second prediction for functional changes downstream of NEU1 also proved to be relevant to rhabdomyosarcoma. The RH30 line has a baseline resistance to doxorubicin which can be weakened by the addition of NEU1. Conversely, RH41 cells are highly susceptible to doxorubicin and can acquire resistance upon upregulation of NEU1. This result points specifically to the efflux of the drug through the lysosome for a number of reasons. First, doxorubicin, like many chemotherapeutics, is a weak base which accumulates in the acid lysosomal compartment. Secondly, neither of these cells lines expresses p-glycoprotein, the traditionally studied method of drug efflux. Instead, we were able to image the trafficking of doxorubicin over a 12 hour period and observed that (1) lysosomes condense around the nucleus in RH41 cells prior to collapse of the cell (2) the lysosomal enzyme cathepsin B translocates to the nucleus prior to apoptosis, (3) the doxorubicin load in these cells is virtually entirely held within the nucleus and (4) resistant cells maintain a mobile fraction of doxorubicin in lysosomes (data not shown).

Alteration of NEU1 status reversed these trends; although it did not completely sensitize the RH30 cells to apoptosis, PARP cleavage could be observed at previously harmless doses of doxorubicin (data not shown). We decided to chemically inhibit lysosomal exocytosis to see if complete inhibition could fully eliminate doxorubicin resistance. To do this we used verapamil, a calcium channel blocker which has previously been considered an inhibitor of p-glycoprotein. However, recent work has shown that this drug can sensitize cells to drug regardless of p-glycoprotein status, suggesting that another mechanism may be the real target of the drug. Because lysosomal exocytosis is dependent on Ca++ influx, chelation of calcium would chemically halt the process and provide a testable change. Rh30 cells co-incubated with verapamil and doxorubicin are fully sensitized to the drug, recapitulating the phenotype of RH41 cells (data not shown). Doxorubicin can be visualized almost exclusively in the nucleus of the verapamil-sensitized RH30 cells, and the elimination of the mobile fraction of the drug is demonstrated (data not shown).

In conclusion, we have presented a model whereby lysosomal exocytosis, as regulated by NEU1, is a critical determinant in cancer cell phenotype (see FIG. 1). The loss of NEU1 results in accumulation of its substrates and alterations to baseline physiology. Two consequences of translocation of lysosomal contents to the extracellular space are degradation of the ECM and efflux of lysosomally-accumulating chemotherapy drugs. Thus, downregulation of NEU1 may be an important predictor for resistance to a class of chemotherapy drugs, including the commonly used doxorubicin, cisplatin, and docetaxel, all of which known to localize at least in part to the lysosome. In addition, NEU1 substrates may represent a rationally designed panel of cancer markers, adding sensitivity to the growing field.

In addition, when taken together, these data predict that genetic deficiency of NEU would render people more vulnerable to acquiring cancers and that those cancers would tend toward aggressiveness.

Example 2: The Role of NEU1 in Chemotherapy Resistance

Background: Rhabdomyosarcoma (RMS) is the most common soft tissue malignancy in children. For children diagnosed with metastatic disease, 3-year survival rates are only about 30%. Systemic chemotherapy is currently the predominant treatment for these patients—and several combination protocols are being used on site here at St. Jude—but drug resistance often blunts response. We have recently developed a novel hypothesis for how drug resistance arises and here propose work to clarify the mechanism. In brief, chemotherapy drugs often accumulate in lysosomes, which are multi-functional acidic organelles. Lysosomes can then be transported to the cell periphery, fuse their membrane with the plasma membrane and release their contents into the extracellular space. This process, called lysosomal exocytosis (LEX), could effectively limit intracellular exposure to drug. Recent work in our lab has identified the lysosomal sialidase NEU1 as a negative regulator of LEX. Without NEU1, its substrate LAMP1 (for Lysosome Associated Membrane Protein) accumulates in lysosomes and aids in their translocation to the plasma membrane. Our preliminary work on RMS cell lines has shown that stable knockdown of NEU1 results in high levels of LAMP1, more LEX, and more drug resistance. Conversely, upregulation of NEU1 results in less LAMP1, less LEX, and reduced drug resistance. Thus, NEU1 downregulation may be advantageous for cancer cells and we have observed such a loss in pediatric RMS tumor samples. Simply administering NEU1 to patients may not be feasible. The NEU1 protein requires complexing with its chaperone, Protective Protein Cathepsin A (PPCA), which may prove to be a rate-limiting step. However, enhancing PPCA is known to significantly boost NEU1 residual activity and this may prove to be a more tractable entry point into clinical control of LEX.

Hypotheses and Specific Aims:

Downregulation of lysosomal exocytosis will enhance RMS response to chemotherapy. We intend to leverage our understanding of LEX to identify opportunities for treatment enhancement in the following two aims. (1) Determine if PPCA upregulation enhances outcome via increasing NEU1 activity. Our lab has developed an AAV-based delivery method for PPCA, which is entering clinical trials as an enzyme replacement approach for children with galactosialidosis. This work suggests that the vector may be relevant to cancer treatment, as well. (2) Determine if targeting LAMP1 results in improved outcome. A small portion of LAMP1 is available to bind to trafficking machinery and facilitate peripheral movement of lysosomes. We will use intracellular delivery of antibody against this sequence to competitively bind and limit movement of the organelles. Success with this methodology will validate the LAMP1 site as a possible target for small molecule development.

Design:

These experiments, as proof-of-principle in vitro work, will occur in well-characterized alveolar RMS cell lines. For Specific Aim 1, dose curves of AAV-PPCA and a panel of chemotherapy drugs (doxorubicin, cisplatin, vincristine) will be tested for induction of apoptosis. The same panel will be used in Specific Aim 2, along with two concentrations of LAMP1 antibody according to established protocols for intracellular delivery. For each intervention, LEX will be measured by assaying levels of lysosomal enzymes in culture media.

Potential Impact:

This work will establish LEX as a determinant of chemotherapy outcome. The suite of proteins we examine, PPCA, NEU1, and LAMP1, may then all be used as markers to characterize a given patient's tumor for LEX capacity. Secondly, the research is expected to indicate possible targeted methods for inhibiting LEX. Not only could this have an impact on cancer treatment generally, it directly addresses the main hurdle in treating pediatric alveolar RMS, particularly once metastasized.

Background:

Chemotherapy resistance is the key problem facing children with metastatic rhabdomyosarcoma. Cancer cells can evade chemotherapy by "pumping" the drug out. For instance, drugs can accumulate in organelles called lysosomes, which can then move to the cell surface, fuse with the cell membrane and release their contents to the outside in a process known as lysosomal exocytosis. Here we examine the main players in this process and study how to inhibit it so that chemotherapeutic drugs remain inside targeted cells and provoke their demise. First, PPCA is a lysosomal protein that guides the enzyme NEU1 into the lysosome and enhances its activity. NEU1 then helps to degrade LAMP1, one of its target substrates. This latter step is important to avoid LAMP1 accumulation in lysosomes, which in turn causes excessive exocytosis. Here we propose testing methods to affect the upstream (PPCA) and downstream (LAMP1) players in order to inhibit exocytosis and thereby allow cancer cells to retain the tested drugs.

Hypotheses and Specific Aims:

Lysosomal exocytosis of drugs decreases effectiveness of chemotherapy but this can be reversed by upregulating PPCA or downregulating LAMP1. Specific Aim 1 will test upregulation of PPCA using a virus delivery method. Specific Aim 2 will test inhibition of LAMP1 through use of an antibody against its binding site so that it cannot facilitate lysosomal movement.

Potential Impact:

This research is expected to establish lysosomal exocytosis as a major determinant of chemotherapy responsiveness. Understanding this mechanism will allow clinicians to predict tumor exocytic capacity and tailor drug combinations/doses accordingly. In addition, we hope to establish specific, potentially druggable targets to inhibit lysosomal exocytosis and enhance patient response.

Example 3: Early Stage Alzheimer's Disease-Phenotype Linked to Deficiency of the Lysosomal Sialidase Neu1

Lysosomal sialidase NEU1 catalyses the hydrolysis of sialo-glycoconjugates by removing their terminal sialic acid residues. In humans, primary or secondary deficiency of this enzyme leads to two clinically similar neurodegenerative lysosomal storage disorders: sialidosis and galactosialidosis. Mice deficient in Neu1 recapitulate the early-onset severe form of sialidosis. We have discovered that loss of Neu1 activity exacerbates the process of lysosomal exocytosis in various cell types by influencing the sialic acid content of Lamp-1. This increases the ability of a pool of lysosomes to dock at the PM and engage in lysosomal exocytosis. In this study we have investigated whether excessive lysosomal exocytosis underlies some of the neurological aspects seen in the brain of $Neu1^{-/-}$ mice. Histopathological examination of the brain of these mice revealed a progressive and time dependent deposition of inclusions/deposits containing APP/Aβ peptide, particularly in the CA3 region of the hippocampus and the adjacent fimbria. The affected regions coincide with sites of high Neu1 expression in wild-type brain. This abnormality was paralleled by abnormal expression of oversialylated Lamp-1 and activated proteases, both features linked to excessive lysosomal exocytosis. These findings represent an example of a spontaneously occurring AD-like phenotype in a mouse model of a neurodegenerative disease and could contribute to the understanding of some of the pathological mechanisms of Alzheimer's disease.

Lysosomal storage diseases (LSDs) comprise a group of more than 50 genetic disorders of lysosomal function, mostly caused by defects in one of the glycan-cleaving lysosomal hydrolases. Enzyme deficiency usually leads to impaired substrates' degradation and to their accumulation in cells of multiple systemic organs and the nervous system. Here we present evidence that mice lacking the lysosomal sialidase Neu1 besides recapitulating the neurodegenerative LSD sialidosis, develop pathological and molecular changes in the brain, which are reminiscent of early-stage Alzheimer's disease (AD). Consequent to Neu1 loss-of-function the combined occurrence of excessive lysosomal exocytosis of neural cells and accumulation of oversialylated Neu1 substrates, including the amyloid precursor protein (APP), underlies this pathogenic cascade. These findings uncover previously unknown molecular mechanisms that could contribute and/or predispose to AD.

The fundamental role of the mammalian lysosomal sialidase NEU1 is to initiate the hydrolysis of sialoglycoconjugates by removing their terminal sialic acids. This activity is crucial to cell homeostasis because genetic defects that alter NEU1 activity disrupt lysosomal metabolism and result in the LSD sialidosis. We have recently identified Neu1 as the only negative regulator of the physiological process known as lysosomal exocytosis (LEX). The latter is a $Ca^{2+}$-dependent, regulated mechanism that involves recruitment/docking of lysosomes to the plasma membrane (PM), a step which is facilitated by the lysosomal associated protein-1 (LAMP-1) and is followed by the fusion of the lysosomal membrane with the PM, and the release of lysosomal luminal content into the extracellular space. We have shown that loss of Neu1 in mouse BM macrophages increases the pool of lysosomes, decorated by oversialylated LAMP-1 on their LM, which are poised to become exocytic. The ensuing exacerbation of this process leads to disease.

Here we tested if Neu1-dependent increase in LEX is the underlying molecular mechanism responsible for neurodegeneration in the mouse model of sialidosis (Neu1$^{-/-}$). We found that Neu1 was present throughout the brain parenchyma but was predominantly expressed in two regions of the wild-type brain: the hippocampus and the choroid plexus (CP) (data not shown). The CP is the exocytic structure of the brain, producing and secreting the cerebrospinal fluid (CSF), and functions as a barrier interface between the blood and the CSF. In the KO mice the CP underwent overt morphologic changes associated with extensive vacuolization and expansion of the lysosomal system (data not shown). This phenotype was accompanied by increased expression of a long-lived oversialylated Lamp-1 (data not shown), a target substrate of Neu1. We have shown this feature in other cells and tissues of the Neu1$^{-/-}$ mice and demonstrated it can be used as read-out of excessive LEX. This was confirmed by measuring the activity of the lysosomal enzymes α-mannosidase and β-hexosaminidase that were both increased in the KO CSF (data not shown).

We reasoned that excessive exocytosis of lysosomal content into the CSF would dramatically alter its composition. We investigated this possibility by comparing the total protein content of the Neu1$^{-/-}$ and Neu1$^{+/+}$ CSF samples using high throughput proteomic analysis. We found many lysosomal enzymes, including cathepsin D and cathepsin B, as well as other proteins to be present in abnormal amounts in the KO CSF (FIG. 2). Increased levels of several of these proteins were also observed in the CP cells of KO animals (data not shown). We postulated that many of the proteins increased in the CSF of KO mice represent undigested substrates of NEU1, which are secreted extracellularly via exacerbated LEX. Notably, multiple proteins differentially regulated in the Neu1$^{-/-}$ CSF have also been identified as possible dementia-predicting biomarkers associated with Alzheimer's disease (FIG. 2). Thus, profound alterations of cellular physiology in one normally Neu1-rich brain region may cause subsequent downstream changes that are highly suggestive of an Alzheimer's-like status when Neu1 is lost. For this reason, we hypothesized that the observed changes in composition of the Neu1$^{-/-}$ CSF would be paralleled by altered characteristics of neural cells in the brain parenchyma. We were intrigued by the observation that the other area of the WT brain expressing Neu1 at high levels is the hippocampus (data not shown), one of the most intensely studied structures of the brain in the AD field. In agreement with our defining paradigm of Neu1 reduction resulting in Lamp-1 accumulation and subsequent excessive LEX, we first looked at Lamp1 and observed a marked increase of this protein throughout the KO brain (data not shown). This was confirmed by immunoblot analysis of brain hippocampal protein extracts that identified increased amount of an oversialylated Lamp-1 (data not shown). Based on these results, we hypothesized that cells in the brain parenchyma of Neu1$^{-/-}$ mice could also exert excessive LEX. Remarkably, Lamp1 was highly expressed in the microglia population (F4/80 staining, data not shown) suggesting that this cell population might be the most exocytic in the brain parenchyma, as previously demonstrated for BM macrophages. We investigated this by culturing WT and KO microglia. We tested their exocytic activity by measuring the levels of active lysosomal hydrolases present in the medium, and found a marked increase of active lysosomal β-hexosaminidase in the medium from KO microglia (data not shown).

We next examined the histopathological characteristics of the KO hippocampus and noticed numerous, abnormal eosinophilic bodies (data not shown). They were variable in size and mostly contained granular proteinaceous material (data not shown). At the EM level, these bodies were identified as swollen dystrophic neurites containing numerous vacuoles of abnormal morphology resembling autophagic vacuoles (data not shown). These features were highly reminiscent of the distended dystrophic neurites associated with AD. Therefore, we began a full characterization of these structures, starting with antibodies reactive to the N-terminal portion of APP and found a time-dependent, progressive accumulation of this protein in the pyramidal neurons of the third subregion of the Cornus ammonis (CA3) of the hippocampus of Neu1$^{-/-}$ brain (data not shown). To test if this phenotype was directly linked to the Neu1 deficiency, we analyzed the sialylation status of APP in the Neu1$^{-/-}$ brain. Evidence for oversialylation of APP came from immunoprecipitation studies; equal amount of hippocampal protein extracts from wild-type and Neu1$^{-/-}$ brain samples were immunoprecipitated with an APP C-terminal antibody and were examined with sambucus nigra lectin (SNA) that binds preferentially to sialic acid attached to terminal galactose with (α-2,6) linkages (data not shown).

It is well established that a slight overexpression of APP is a risk factor for the development of AD and duplication of the APP locus in familial AD and Down syndrome patients is the basis of early onset AD. We therefore tested a number of canonical histological markers commonly applied for the diagnosis of AD in the brain of Neu1$^{-/-}$ mice. Swollen dystrophic neurites were readily detected with thioflavin S fluorescence suggesting they were structurally close to amyloid deposits (data not shown). Modified Bielschowsky silver stain also highlighted scattered silver-positive neuritic structures (data not shown), not found in aged matched WT mice. The APP accumulating neurites were also immunoreactive with antibodies recognizing APP/Aβ (data not shown), and were positive when stained with an antibody against the β-amyloid isoform ending at the 42nd amino acid (Aβ42) (data not shown). Most importantly, almost all the APP+ dystrophic neurites were immunostained with ubiquitin, neurofilaments and tau antibodies indicating the presence of protein aggregates and extensive cytoskeletal abnormalities in these structures (data not shown). We believe that APP accumulation in these dystrophic neurites contributes to the formation of toxic amyloid peptides (Aβ) because quantitative determination of Aβ40 and Aβ42(43) showed elevated Aβ peptides in the Neu1$^{-/-}$ brain (data not shown). Based on these data, we conclude that Neu1 deficiency is directly linked to early pathogenic events observed in AD.

The APP+ neurites may represent early events in the pathogenesis of the neuropil threads characterized by true amyloid and plaque deposition. APP overexpression in neurons or neurites may be toxic and cause degeneration with release of this protein. Exocytic microglia could then contribute to the pathogenic process by releasing into the extracellular space activated lysosomal enzymes that progressively process the APP producing toxic Aβ peptides.

Here we have identified a novel mechanism orchestrated by deficiency of lysosomal Neu1 that promotes deposition of oversialylated APP which in turn may constitute a risk factor for the development of late-onset non-familiar AD. The discovery of novel putative Neu1 substrates, including APP, and the occurrence of deregulated LEX in the brain/CSF

Example 4: Metabolic Control of Chemotherapy Resistance and Metastasis

Summary

The dual dangers of cancer progression are chemotherapy resistance and metastatic growth, both of which depend on the metabolic status of tumor cells. Here, we demonstrate that the lysosomal sialidase NEU1 plays a defining role in the development of both phenotypes by negatively regulating the physiological process of lysosomal exocytosis. Cancer cells use this mechanism to sequester and purge lysosomotropic chemotherapeutics, thereby developing drug resistance. Moreover, exocytosed active lysosomal enzymes from tumors degrade the extracellular matrix of surrounding tissue, compromising its ability to contain tumor spread. Tumor-prone mice haploinsufficient for Neu1 develop highly aggressive rare forms of cancer, confirming a role for NEU1 in controlling malignancy. In addition, downregulation of NEU1 is common in multiple human cancers. We propose that NEU1 functions as a bona fide tumor suppressor by restraining lysosomal exocytosis in cancer cells, precluding the development of a drug resistant and invasive phenotype.

Highlights
- Lysosomal sialidase NEU1 negatively regulates lysosomal exocytosis in cancer cells
- Increased lysosomal exocytosis confers chemotherapy resistance and invasiveness
- Neu1 haploinsufficiency potentiates tumor growth and spread in $Arf^{-/-}$ mice
- Downregulation of NEU1 is observed in multiple human cancers Introduction The lysosomal glycosidase N-acetyl-α-neuraminidase 1 (NEU1) is the most abundant and widely expressed mammalian sialidase. Its canonical function is to remove α2,6- or α2,3-linked terminal sialic acids from the saccharide chains of glycoproteins, glycolipids (gangliosides), oligosaccharides, and polysaccharides (Monti et al., 2010). Genetic deficiency of NEU1 results in impaired catabolism of sialic acids on its target substrates, which in turn, affects countless cellular functions and leads to the loss of cell and tissue homeostasis. The pathogenic effects of NEU1 loss of function are obvious in the lysosomal storage disease sialidosis, a severe neurosomatic condition in children and adolescents that affects most of the systemic organs and the nervous system (d'Azzo, 2009; Thomas, 2001).

In cancer, altered sialylation of glycoconjugates at surface membranes is considered a central determinant of the neoplastic process, though it is often unclear how changes in glycan composition result in aberrant biological outcome (Varki et al., 2009; Wang, 2005). This dynamic posttranslational modification involving a charged sugar moiety can greatly modify the biochemical and functional properties of proteins and lipids, thereby affecting cell-cell and cell-extracellular matrix (ECM) interactions, cell migration and adhesion patterns, intracellular signaling and metastatic potential (Varki et al., 2009; Wang, 2005; Hedlund et al., 2008; Uemura et al., 2009). Excessive sialic acid content can result from two opposing processes, upregulation of the synthetic enzymes sialyltransferases that control the regulated transfer of sialic acids to nascent oligosaccharide moieties; and loss of activity of the sialidases that affect the same sugar nucleotide linkages. For example, a compelling recent study has implicated the overexpression of the sialyltransferase ST6GalNAc-V in the enhanced metastatic potential of breast cancer cells, most likely through abnormal sialylation of as yet unidentified proteins (Bos et al., 2009). One could argue that loss or downregulation of NEU1 would necessarily result in abnormal processing of sialylated substrates, making the catabolic arm of this post-translational modification as relevant for cancer progression and growth. In fact, changes in the expression levels of sialidases have been associated with cell migration and metastasis (Kato et al., 2001; Miyagi et al., 1994; Sawada et al., 2002; Uemura et al., 2009).

A previously unknown function for the sialidase NEU1 with great relevance to cancer has recently been discovered: that of negative regulator of lysosomal exocytosis (LEX) (Yogalingam et al., 2008). This ubiquitous, calcium-regulated physiological process entails the recruitment to the cytoskeletal network of a selective pool of lysosomes that dock at the plasma membrane (PM); their limiting membrane then fuses with the PM in response to calcium influx and their luminal content is released extracellularly (Bossi and Griffiths, 2005; Andrews, 2000; Rodriguez et al., 1997). NEU1's function in this process is mediated via the lysosomal associated membrane protein 1 (LAMP1), a natural substrate of NEU1 (Yogalingam et al., 2008), which was previously implicated in the peripheral movement of lysosomes (Reddy et al., 2001). LAMP1 is a heavily glycosylated and sialylated structural component of the lysosomal membrane whose regulated turnover is considerably delayed when the protein is oversialylated due to loss of NEU1 activity (Yogalingam et al., 2008). Long-lived oversialylated LAMP1 changes the lysosomal membrane topology and trafficking, thereby increasing the number of exocytic lysosomes docked at the PM ready to fuse and secrete their contents (Yogalingam et al., 2008).

Recent reports have made explicit calls for more attention to the area of regulated exocytosis and cancer (Chan and Weber, 2002; Hendrix et al., 2010; Palmer et al., 2002). The involvement of this process as a mediator of malignant growth and invasiveness has been postulated in view of the deregulated activities of vesicular trafficking effectors observed in some cancers (Hendrix et al., 2010; Palmer et al., 2002). Exocytosis can impact at least two critical areas of malignant progression: abnormal remodeling of the ECM and promoting the efflux of chemotherapeutic agents, many of which are lysosomotropic. Anthracyclines, cisplatin, and sunitinib are examples of such drugs that have been directly visualized in lysosomes, whose trafficking could greatly influence the intracellular exposure to the drug (Gotink et al., 2011; Hurwitz et al., 1997; Safaei et al., 2005). The degradation and remodeling of the ECM has been attributed to the presence of lysosomal proteases in the extracellular environment and has been strongly correlated with tumor invasiveness and metastasis (Khan et al., 1998a; Khan et al., 1998b; Matarrese et al.).

In the present study we demonstrate that downregulation of NEU1 activity levels in invasive cancer results in the accumulation of an oversialylated LAMP1 and in enhanced lysosomal exocytosis. The combination of these processes initiates a cascade of events that favor tumor progression, invasiveness and resistance to chemotherapeutic drugs. These results establish that NEU1 functions as a tumor suppressor by negatively regulating lysosomal exocytosis.

Results

NEU1 Expression is Inversely Related to Lysosomal Exocytosis in Rhabdomyosarcoma Cell Lines Rhabdomyosarcoma (RMS), which arises in skeletal muscle, is the most common soft-tissue malignancy in children and adolescents (Ognjanovic et al., 2009). This cancer is classified into two subtypes, embryonal RMS, which typically has a favorable prognosis, and alveolar RMS, which is associated with poor prognosis (Ognjanovic et al., 2009). RMS is treated primarily with surgical resection and chemotherapy; common complications are metastases and chemotherapy resistance, both of which could result from excessive LEX.

To investigate the role of NEU1 in regulating LEX in cancer cells, we chose two human RMS cell lines that express different amounts of NEU1. RH41 and RH30 cells were both derived from alveolar RMS tumors (Houghton et al., 2007). Affymetrix mRNA microarray analysis of NEU1 expression showed that RH41 cells express a relatively high level of NEU1 mRNA compared with that expressed by RH30 cells. We confirmed this finding using semiquantitative and real-time PCR (data not shown). The mRNA results correlated well with the levels of NEU1 activity (data not shown). Immunofluorescent labeling also revealed a typical lysosomal distribution of NEU1 in both cell lines, but expression was markedly higher in the RH41 cells (data not shown).

On the basis of the different patterns of NEU1 expression in the RMS cell lines, we characterized their LEX profiles. Western blot analysis of LAMP1 confirmed that the protein was more abundant in the low-NEU1 RH30 cells and had a higher molecular weight, which was indicative of increased sialic acid content (data not shown). In addition, using confocal immunofluorescence, we observed a LAMP1$^+$ signal on the cell surface of nonpermeabilized RH30 cells but not on RH41 cells. This suggests an enhanced tendency of a LAMP1-marked pool of lysosomes in the low-NEU1 cells to dock at and fuse with the PM, leading to accumulation of LAMP1 at that site (data not shown). We further monitored lysosomal trafficking in real time by capturing confocal images of lysotracker red-tagged puncta. In RH30 cells, lysosomes were preferentially captured at the cell periphery and continuously dispatched from the cell center outward; in contrast, RH41 cells had virtually no lysosomes residing outside the perinuclear space (data not shown). Total internal reflection (TIRF) microscopic analysis confirmed that the peripheral lysosomes in RH30 cells were in close proximity to the PM. Live RH30 cells stained with lysotracker green showed evidence of signal localization within the range of TIRF-sensing, but RH41 cells did not (data not shown). Finally, we measured the extracellular activity of the lysosomal enzyme β-hexosaminidase (β-Hex) in culture medium from each cell line as a measure of released lysosomal content. RH30-conditioned medium contained considerably more β-Hex than did RH41-conditioned medium, in inverse relation with their respective levels of NEU1 (data not shown).

NEU1 Expression Levels Influence the Extent of Lysosomal Exocytosis

To pinpoint the primary role of NEU1 in the exocytic phenotype, we engineered stable NEU1-modified clones of the 2 RMS cell lines by using retroviral vectors. Modified RH30 cells overexpressing NEU1 (RH30$^{NEU1}$) and RH41 cells with silenced NEU1 (RH41$^{shNEU1}$) were first characterized for their NEU1 protein levels and activity to confirm the successful reversion of their NEU1 expression patterns with respect to the corresponding empty-vector controls (data not shown). LEX was then measured in both modified cell lines and corresponding controls using 3 parameters: LAMP1 levels, TIRF analysis, and enzyme activities in conditioned media. LAMP1 levels were inversely proportional to the levels of NEU1 activity in the modified lines (data not shown). In addition, LAMP1$^+$ immunofluorescence was notably localized to the cell periphery of RH41$^{shNEU1}$ cells and control RH30$^{empty}$ cells compared to their high-NEU1 counterparts (RH30$^{NEU1}$; RH41$^{empty}$) (data not shown). TIRF imaging confirmed the peripheral trafficking of lysosomes and their tendency to cluster at the termini of cell extensions in the RH41$^{shNEU1}$ cells (data not shown). In contrast, this feature was lost in RH30$^{NEU1}$ cells (data not shown).

Finally, the activity of lysosomal β-Hex was assayed in the culture medium from each modified cell line and control. The media from the low-NEU1 cells contained significantly more β-Hex activity (data not shown). Together, these results demonstrate that the NEU1 status of a cell is sufficient to determine its LEX phenotype.

Increased Lysosomal Exocytosis Correlates with Doxorubicin Resistance

We next looked at the functional ramifications of NEU1 control over LEX in relation to the response of the parental cell lines to chemotherapeutic drugs. RH41 and RH30 cells have been shown to respond to a variety of antineoplastic therapy in markedly different way (Houghton et al., 2007; Petak et al., 2000). We found that upon exposure to doxorubicin (DOXO), RH41 cells readily apoptosed; RH30 cells were resistant to treatment (data not shown). To link these phenotypes to the level of NEU1 activity in these cells, we first confirmed that DOXO was concentrated in their lysosomes. The native red fluorescence of the drug colocalized with lysotracker green, revealing that DOXO-loaded lysosomes were present in both parental RMS cell lines, albeit differently distributed throughout the cytoplasm (data not shown). Specifically, after 2 hours of treatment, DOXO-loaded lysosomes in RH41 cells clustered in the perinuclear region, but those in RH30 cells did not (data not shown). Overnight live imaging of lysosome trafficking upon DOXO exposure confirmed these trends (data not shown). The intracellular visualization of DOXO at 4 hours confirmed that the drug was primarily concentrated in the nuclei of RH41 cells, while in the RH30 cells a fraction of the drug remained lysosomal (data not shown).

The increase in LEX observed in the low-NEU1 RH30 cells could promote the efflux of DOXO, hence making the cells insensitive to treatment. This prediction was further supported by the fact that these cells do not express the multidrug-resistance protein 1 (p-glycoprotein 1) that functions in a well-known cellular mechanism for evading drug toxicity (Cocker et al., 2000). By capturing and quantifying the effluxed red fluorescence from the RH30 culture medium, we showed that DOXO was indeed released from these cells (data not shown).

Finally, we generated DOXO dose response curves in both parental cell lines and the modified lines to examine the differences in their apoptotic responses. Immunoblots of the cleaved poly (ADP-ribose) polymerase (PARP), a canonical apoptotic marker, were used for this purpose (data not shown). The RH41$^{shNEU1}$ cells were more resistant to apoptosis than were the corresponding unmodified cells (data not shown). In contrast, the RH30$^{NEU1}$ cells were more sensitive to DOXO than were their unmodified controls (data not shown). In view of these results, we tested whether inhibiting LEX with the calcium channel blocker verapamil would sensitize the parental RH30 cells.

Verapamil is a p-glycoprotein inhibitor, but it also inhibits drug efflux in the absence of p-glycoprotein, which suggests an alternative efflux mechanism (Chiu et al., 2010). Because LEX depends on calcium influx, we hypothesized that this commonly used calcium channel blocker would inhibit this process. Upon co-treatment of the RH30 cells with verapamil and DOXO, the lysosomes accumulated the drug and clustered in the perinuclear region (data not shown). The cells then underwent apoptosis, as measured by PARP cleavage and morphological analysis (data not shown).

NEU1-Dependent Exacerbation of Lysosomal Exocytosis Increases the Invasive Capacity of Cancer Cells The second feature of cancer cells that we predicted would be affected by excessive LEX is invasiveness, because degradation of the ECM would compromise the tissue's ability to contain the tumor. The release of active lysosomal resident proteases, particularly cathepsin B, correlates with basement membrane perforation and metastasis (Khan et al., 1998a; Khan et al., 1998b; Matarrese et al.).

We determined that NEU1 levels, and in turn extent of LEX, in tumor cells are linked to their invasive properties. For this purpose, we used the parental RH41 and RH30 lines as representative of high- and low-NEU1 cells, respectively. The ex vivo invasive potentials of these cells were measured using denucleated peritoneal basement membranes (Marshall et al., 2011) obtained from either wild-type or Neu1-knockout mice (data not shown). Because the Neu1-knockout mouse is a model of constitutive, excessive LEX, its tissues and ECM already have been subjected to progressive environmental stresses that mimic tumor-adjacent tissue (Yogalingam et al., 2008; Zanoteli et al., 2010). Compared to high-NEU1 RH41, the low-NEU1 RH30 line more successfully invaded the wild-type substrate (data not shown). However, the peritonea from Neu1-knockout mice were significantly more vulnerable to invasion from either RMS cell line than were the wild-type peritonea (data not shown). Notably, the high-NEU1 RH41 cells seeded on a Neu1-knockout peritoneum were as invasive as the RH30 cells on a wild-type peritoneum, suggesting that intrinsic LEX had conditioned the otherwise healthy tissue for cancerous invasion (data not shown). The invasive properties of the RMS cell lines were further evaluated in the Neu1-knockout peritoneum sections by immunohistochemical visualization of the basement membrane components, laminin and collagen IV, both of which are cathepsin B substrates (Buck et al., 1992). Tissue exposed to RH30 cells underwent more destruction/remodeling than did tissue exposed to RH41 cells (data not shown).

The inverse relationship between NEU1 activity and invasive potential of the RMS cells suggested that this is a general mechanism that may be used by other cancers. We, therefore, characterized other tumor cell lines, in terms of their invasive potential and NEU1 status. We chose the Ewing sarcoma cell lines, EW8 and SKNEP1, for their divergent NEU1 levels. Similar to the RMS cell lines, the low-NEU1 SKNEP1 cells accumulated oversialylated LAMP1, were resistant to DOXO, and more successfully invaded matrigel and peritoneal basement membranes than did the high-NEU1 DOXO-sensitive EW8 cells (data not shown). We also analyzed the colon carcinoma cell lines, SW480 and SW620, because of their well-characterized derivation (Leibovitz et al., 1976): SW480 cells are from a primary colon carcinoma; SW620 cells are from a metastatic recurrence. The latter cells were also shown to be more resistant to anti-neoplastic drugs than SW480 cells (Walker et al., 2010), and we found that they downregulated NEU1 activity. This was also paralleled by a drastic increase in LAMP1 levels compared to that in SW480 (data not shown).

The NEU1 Status of RMS Cells is the Primary Determinant of Differences in Their Invasive Capacity To determine how NEU1 levels influence the invasiveness of RMS cells, we seeded the RH41$^{shNEU1}$ and RH30$^{NEU1}$ cells, along with the empty-vector controls, on a matrigel substrate consisting primarily of laminin and collagen IV. After the cells were maintained in culture for 2 days, the matrigel plugs were fixed and processed to visualize the ingress of cells into the substrate. The cells with low-NEU1 activity (RH41$^{shNEU1}$ and RH30$^{empty}$) successfully invaded the matrigel, whereas those with high-NEU1 activity did not (data not shown). These results established that the NEU1 status of these cancer cells is sufficient to predict their ability to invade a standardized substrate.

Neu1-Deficient Mice Generate More Aggressive Cancers in a Tumor-Prone Model

Using Neu1-heterozygous mice crossed into a tumor-prone model, the Arf-knockout mouse (Kamijo et al., 1999), we tested whether excessive LEX affects malignant invasion in vivo. Two groups of mice were compared for tumor outcome. The first group, Arf$^{-/-}$/Neu1$^{+/+}$ mice, produced a range of tumors that reflected the type of neoplasms previously reported in Arf single knockouts (Kamijo et al., 1999). Typical tumors in Arf-knockout mice younger than 10 months are poorly differentiated sarcomas, though gliomas, lymphomas, and carcinomas have been observed in low frequency (Kamijo et al., 1999). Tumors in these mice arose at the average age of 9 months and were typically focal (data not shown). The second group consisted of mice with an Arf$^{-/-}$/Neu1$^{+/-}$ genotype. We anticipated that the low-Neu1 activity in these mice would encourage faster, more virulent growth of any developing tumors. This was indeed the case; the mice developed tumors at an average age of 6 months, which was significantly earlier than that seen in the Arf single knockouts ($p=0.029$). In addition, tumor growth was so aggressive that mice were quickly rendered moribund. These tumors were often locally invasive and achieved large volumes in a short time span. In one case, the tumor was fulminantly metastatic (data not shown). Tumors in the Neu1-heterozygous mice were sometimes pleomorphic, not resembling those commonly seen in genetically-engineered mice. Two such malignancies had morphologic and immunohistochemical features of the rhabdoid/epithelioid sarcoma-like group of tumors. They contained rhabdoid-type cells positive for both vimentin and cytokeratin 8, cytoskeletal markers for mesenchymal and epithelial cells, respectively (data not shown). This group of tumors has not, to our knowledge, been reported in mice, and in humans is associated with aggressive biological behavior and a poor prognosis (Oda and Tsuneyoshi, 2006).

One additional small cohort of mice, Arf$^{-/-}$/Neu1$^{-/-}$ double knockouts, was generated during this breeding program. Very few mice of this genotype were born (17 of 122 total mice), and the mice succumbed to sialidosis-related mortality early in life. For these reasons, we did not include this cohort in the statistical analysis, though we report the outcomes of the few mice that developed tumors, one metastatic, before the sialidosis became fatal (data not shown).

The easily characterized tumors that arose in the Arf$^{-/-}$/Neu1$^{+/+}$ mice provided an opportunity to investigate the expression of Neu1 in tumors compared to their cells of origin. We observed a loss of Neu1 immunostaining in tumors compared to that in normal tissue from the same mouse. This difference was seen in a carcinoma and a sarcoma (data not shown), supporting the notion that downregulation of Neu1 offers selective advantages to tumor growth.

Loss of NEU1 in Human Cancer

We reasoned that the pattern of Neu1 expression in the Arf$^{-/-}$/Neu1$^{+/+}$ mice might be reproduced in patients with cancer, who should have normal NEU1 activity. We first probed human RMS tissue samples of the more common embryonic subtype for the levels of NEU1 compared to healthy skeletal muscle controls. NEU1 was, in fact, downregulated in 10 of 12 (83.3%) RMS samples (data not shown). Four of the 10 showed a complete absence of NEU1 staining (data not shown). To further characterize the physiological impact of NEU1 downregulation, we assessed the levels of its substrate LAMP1. LAMP1 immunohistochemistry revealed a strong upregulation of this protein in 7 of 12 (58.3%) samples, including all 4 of those with complete loss of NEU1 (data not shown). We next decided to repeat this analysis on pancreatic ductal adenocarinoma samples to gauge how common NEU1 downregulation is across cancer types. Again, 10 of 12 (83.3%) samples showed a loss of NEU1 compared to the originating ductal cells (data not shown). LAMP1 staining was also performed and replicated the results seen in RMS, with 7 of 12 (58.3%) carcinoma samples showing upregulation (data not shown). Collectively, these results suggest that downregulation of NEU1 is a commonly employed strategy in cancer cells, often coupled to accumulation of LAMP1 and concomitant exacerbation of LEX.

Discussion

In this study we provide evidence that the downregulation of NEU1 and consequent enhanced LEX imparts at least two crucial advantages to cancer cells: resistance to lysosomotropic chemotherapeutic agents and the ability to become expansive and infiltrative. These findings suggest a tumor-suppressor function for NEU1.

The regulated expression of this pleiotropic lysosomal enzyme affects two cellular processes, sialylation of glycoconjugates and the extent and type of lysosomal trafficking, both of which have been consistently invoked to explain tumor cell behavior in vivo (Hendrix et al., 2010; Varki, 2009). Thus far, oversialylation has been largely attributed to upregulation of the biosynthetic enzymes sialyltransferases (Dall'Olio and Chiricolo, 2001). For instance, ST6GalNAc-I [(α-N-acetyl-neuraminyl-2,3-β-galactosyl-1,3)-N-acetylgalactosaminide α-2,6-sialyltransferase-I] is thought to contribute to the generation of the mucin-associated sialyl-Tn antigen, a marker of metastatic carcinoma (Heimburg-Molinaro et al., 2011; Marcos et al., 2011), and ST6GalNAc-V imparts metastatic potential to breast cancer (Bos et al., 2009). Both of these sialyltransferases catalyze the transfer of sialic acids in a2,6-linkage to GalNAc (N-acetyl-galactosamine) residues found in glycoproteins and glycolipids, a process that may be readily reversed by NEU1. We propose that diminished or deficient NEU1 activity impinges on cancer cells in a manner that is equivalent to sialyltransferase overexpression, thereby causing impaired sialic acid catabolism of target NEU1 substrates. It is noteworthy in this respect that a query of the Oncomine database (Finak Breast www.oncomine.org/resource/main.html) revealed a substantial upregulation (p<0.01) of at least 3 α2,6-sialyltransferases, including the ST6GalNAc-I enzyme, as well as ST6GalNAc-III and ST6Gal-II. We found that these inversely correlated with NEU1 expression, which was itself significantly downregulated (p<0.01). The opposing expression levels of these enzymes in cancer could cause an underappreciated double insult on the cellular regulation of sialylation.

Our study identified over-sialylated LAMP1 as a critical regulator of LEX in cancer, providing both a marker for excessive LEX and a possible target for inhibiting this process. Deregulation of other proteins involved in vesicular trafficking has been observed in some cancers. Namely, upregulation of two LEX effectors, Rab27B and BAIAP3, was shown to enhance the metastatic growth and cell proliferation of breast cancer and desmoplastic small round cell tumors, respectively (Hendrix et al., 2010; Palmer et al., 2002), suggesting the involvement of an exocytic mechanism in neoplasia (Chan and Weber, 2002). Here we present evidence to definitively link LEX to the important cancer phenotypes of invasiveness and drug resistance.

The suggestion that lysosomal trafficking influences multidrug resistance has been proposed, with some reviews explicitly calling for more research in this area (Castino et al., 2003; Groth-Pedersen, 2010). An early report noted that DOXO is concentrated into acidic vesicles that could exocytose their contents (Klohs and Steinkampf, 1988). Later, vinblastine was observed to specifically accumulate in lysosomes and be effluxed in conjunction with lysosomal enzymes (Warren et al., 1991). The study on how chemotherapeutics are released from tumor cells has largely focused on the upregulation of p-glycoprotein or other ABC transporters (Coley, 2010). However, specific inhibitors of these pumps have often proven unsuccessful in clinical trials, suggesting that other mechanisms of efflux are involved (Broxterman et al., 2009; Coley, 2010). Again, our search of the Oncomine database revealed supportive evidence for NEU1 mediating an important resistance mechanism. While p-glycoprotein expression was not significantly different (p=0.81) between responders and non-responders to the 5-FU and the topoisomerase poison irinotecan in a data set for metastatic colon cancer, NEU1 expression was strongly downregulated (p=0.0064) in the resistant patients (Graudens Colon data set at the website located at oncomine.org/resource/main). Here we have established that the DOXO-resistant RMS cell line effluxes DOXO, despite lacking the p-glycoprotein. The same cells can then be made more sensitive to DOXO by inhibiting LEX, either by upregulating NEU1 or using the calcium channel blocker verapamil. Thus, lysosomotropic drug efflux is under the control of NEU1, as a critical determinant of LEX.

NEU1-regulated LEX also has a direct influence on the invasive/metastatic potential of cancer cells. First, otherwise healthy tissue subjected to excessive LEX, as in the case of Neu1-knockout mice, is more susceptible to cancer cell invasion. Second, the level of NEU1 in cancer cells is inversely related to their invasive potential. Third, the combined loss of NEU1 in the tumor and the surrounding tissue in vivo creates the conditions for highly aggressive cancers. The Arf$^{-/-}$/Neu1$^{+/-}$ mice developed various tumors, including highly aggressive, rare rhabdoid/epithelioid-like sarcomas of uncertain histogenesis. Because no mouse model has been identified for this type of cancer, the spontaneous generation of these tumors offers a possible window of opportunity into the study of these rare and deadly malignancies.

In addition to low-NEU1 status being a potential risk factor in the development of cancer, neoplastic transformation may place selective pressure on tumor cells to downregulate NEU1, as demonstrated by the loss of Neu1 expression in the tumors developed by Arf single-knockout mice. NEU1 activity levels in the normal human population range widely, with as-yet-unknown ramifications. It is predictable that individuals with low NEU1 activity, i.e., those with the type I sialidosis, would be more vulnerable to cancer than are healthy controls. This appears to be the case; Yagi and colleagues recently reported different neoplastic malignancies in three siblings with type I sialidosis and suggested a link between these occurrences and NEU1 deficiency (Yagi et al., 2011).

We show here that NEU1 is robustly downregulated in malignant tissues from human RMS and pancreatic adenocarcinoma compared to unmatched healthy tissue. Whether this is due to a preexisting deficiency or to a transformation-related change is unknown and deserves further attention. In either case, reduced NEU1 expression may be an informative marker, both because of the consistency of its down-regulation and because of the physiological ramifications of its loss. Coupled to accumulation of substrate, NEU1 loss could function as a predictor of excessive LEX and its important consequences of increased invasiveness and drug resistance in tumors. Such information may help to shape treatment decisions and to optimize the rational design of new drug combination trials.

Experimental Procedures

Animals

Neu1$^{+/-}$ mice were bred with Arf$^{-/-}$ mice (kindly provided by Dr. Charles Sherr). The colony was expanded for 1 year, during which time the birth rates and tumor burdens were documented. Full necropsies were performed by the St. Jude Veterinary Pathology Core. All mouse experiments were performed according to animal protocols approved by our institutional Animal Care and Use Committee and NIH guidelines.

Cell Culture

The RMS cell lines RH41, RH30 and Ewing sarcoma cell lines EW8, and SKNEP-1 were kindly provided by Drs. Gerard Grosveld and Andrew Davidoff. These cell lines were characterized by the Pediatric Preclinical Testing Program at St. Jude Children's Research Hospital (Houghton et al., 2007). SW480 and SW620 adenocarcinoma colon cancer cell lines were obtained from ATCC. Cells were maintained in DMEM or RPMI (Invitrogen) media supplemented with Glutamax (Sigma), penicillin and streptomycin (Invitrogen), and 10% cosmic calf serum (Hyclone). Puromycin-resistant clones were selected and maintained in media supplemented with puromycin (2 μg/mL, Sigma).

Antibodies and Reagents

We used commercial antibodies: anti-LAMP1 (Sigma), anti-laminin (Sigma), anti-α/β tubulin and anti-cleaved PARP (Cell Signaling). Polyclonal anti-NEU1 antibody has been previously described (Bonten et al., 2004). Verapamil (50 μM, Sigma) and DOXO (3 μg/mL, LKT Laboratories) were added to the culture media. Lysotracker Green DND-26 and Lysotracker Red DND-99 were obtained from Invitrogen and applied per the manufacturer's instructions.

Immunoblotting

Tissue and cell-pellet preparation, Western blotting, and data analyses were performed as previously described (Zanoteli et al., 2010).

Immunohistochemistry and Fluorescent Microscopy

Immunohistochemical analyses of mouse tissue sections and microarray analyses of human tissue samples (US BioMax, Inc.) were performed as previously described (Yogalingam et al., 2008). The use of human tissue samples was approved by our Institutional Review Board.

Enzyme Assays

NEU1 and β-Hex enzymatic activities were measured with the appropriate fluorimetric substrates (Sigma) and normalized to BCA protein concentrations (Pierce Biotechnology) as described previously (Yogalingam et al., 2008).

Stable Clone Cell Lines

RH30 cells were transduced with the pBABE-puro retroviral vector (AddGene), either unmodified or containing the human NEU1 cDNA. Transduced cells were selected with puromycin (2 μg/mL), according to the predetermined sensitivity of the cell line, and were maintained in 0.5 μg/mL selection medium. RH41 cells were transfected with a panel of NEU1 shRNA plasmids (RHS4533-NM000434, Open Biosystems) or the accompanying empty vector control. The cells were selected with puromycin and maintained under selection medium.

Doxorubicin Efflux Assay

Cells were plated and maintained at 50% confluency. The next day, they were treated with medium containing 3 μg/mL DOXO for 2 hours. Treated cells were then washed 3 times with PBS and cultured in DOXO-free medium for an additional 2 hours, to allow efflux of the drug into fresh medium. The conditioned medium was then centrifuged at 1000 rpm (867×g) for 5 minutes and a 500 μL aliquot was spun through an ULTRAFREE-MC 0.1 μm Eppendorf centrifugal filter (Millipore) to capture the effluxed drug. The filter was then placed on a microscopic slide and images of the red fluorescence filter were taken on a Nikon C1 microscope.

Invasion Assays

Peritoneal sections were harvested from wild-type or Neu1-knockout mice of matched ages and mounted over transwell inserts (Fisher), as previously described (Marshall et al., 2011). A total of 250,000 RMS cells per line were then overlaid onto the peritoneal preparation and kept in culture for 8 days.

In a separate set of experiments, 250,000 RMS cells per line were seeded onto 200 μL matrigel in a transwell dish and maintained in culture for 2 days, as previously described (Sabeh et al., 2009).

Statistics

Data are expressed as mean±standard deviation (SD) and were evaluated using the Student's t-test for unpaired samples. P-values less than 0.05 were considered statistically significant.

REFERENCES

Bos, P. D., Zhang, X. H., Nadal, C., Shu, W., Gomis, R. R., Nguyen, D. X., Minn, A. J., van de Vijver, M. J., Gerald, W. L., Foekens, J. A., et al. (2009). Genes that mediate breast cancer metastasis to the brain. Nature 459, 1005-1009.

Broxterman, H. J., Gotink, K. J., and Verheul, H. M. (2009). Understanding the causes of multidrug resistance in cancer: a comparison of doxorubicin and sunitinib. Drug Resist Updat 12, 114-126.

Buck, M. R., Karustis, D. G., Day, N. A., Honn, K. V., and Sloane, B. F. (1992). Degradation of extracellular-matrix proteins by human cathepsin B from normal and tumour tissues. Biochem J 282 (Pt 1), 273-278.

Castino, R., Démoz, M., and Isidoro, C. (2003). Destination 'lysosome': a target organelle for tumour cell killing? J Mol Recognit 16, 337-348.

Chan, A. M., and Weber, T. (2002). A putative link between exocytosis and tumor development. Cancer Cell 2, 427-428.

Chiu, L. Y., Ko, J. L., Lee, Y. J., Yang, T. Y., Tee, Y. T., and Sheu, G. T. (2010). L-type calcium channel blockers reverse docetaxel and vincristine-induced multidrug resistance independent of ABCB1 expression in human lung cancer cell lines. Toxicol Lett 192, 408-418.

Cocker, H. A., Pinkerton, C. R., and Kelland, L. R. (2000). Characterization and modulation of drug resistance of human paediatric rhabdomyosarcoma cell lines. Br J Cancer 83, 338-345.

Coley, H. M. (2010). Overcoming multidrug resistance in cancer: clinical studies of p-glycoprotein inhibitors. Methods Mol Biol 596, 341-358.

d'Azzo, A., Kolodny, E. H., Bonten, E., Annunziata, I. (2009). Hematology of Infancy and Childhood (Philadelphia, Pa., Saunders Elsevier).

Dall'Olio, F., and Chiricolo, M. (2001). Sialyltransferases in cancer. Glycoconj J 18, 841-850.

Gotink, K. J., Broxterman, H. J., Labots, M., de Haas, R. R., Dekker, H., Honeywell, R. J., Rudek, M. A., Beerepoot, L. V., Musters, R. J., Jansen, G., et al. (2011). Lysosomal sequestration of sunitinib: a novel mechanism of drug resistance. Clin Cancer Res 17, 7337-7346.

Groth-Pedersen, L., Jaattela, M. (2010). Combating apoptosis and multidrug resistant cancers by targeting lysosomes. Cancer Letters doi:10.1016/j.canlet.2010.05.021.

Hedlund, M., Ng, E., Varki, A., and Varki, N. M. (2008). alpha 2-6-Linked sialic acids on N-glycans modulate carcinoma differentiation in vivo. Cancer Res 68, 388-394.

Heimburg-Molinaro, J., Lum, M., Vijay, G., Jain, M., Almogren, A., and Rittenhouse-Olson, K. (2011). Cancer vaccines and carbohydrate epitopes. Vaccine 29, 8802-8826.

Hendrix, A., Westbroek, W., Bracke, M., and De Wever, O. (2010). An ex(o)citing machinery for invasive tumor growth. Cancer Res 70, 9533-9537.

Hinek, A., Bodnaruk, T. D., Bunda, S., Wang, Y., and Liu, K. (2008). Neuraminidase-1, a subunit of the cell surface elastin receptor, desialylates and functionally inactivates adjacent receptors interacting with the mitogenic growth factors PDGF-BB and IGF-2. Am J Pathol 173, 1042-1056.

Houghton, P. J., Morton, C. L., Tucker, C., Payne, D., Favours, E., Cole, C., Gorlick, R., Kolb, E. A., Zhang, W., Lock, R., et al. (2007). The pediatric preclinical testing program: description of models and early testing results. Pediatr Blood Cancer 49, 928-940.

Hurwitz, S. J., Terashima, M., Mizunuma, N., and Slapak, C. A. (1997). Vesicular anthracycline accumulation in doxorubicin-selected U-937 cells: participation of lysosomes. Blood 89, 3745-3754.

Kamijo, T., Bodner, S., van de Kamp, E., Randle, D. H., and Sherr, C. J. (1999). Tumor spectrum in ARF-deficient mice. Cancer Res 59, 2217-2222.

Kato, T., Wang, Y., Yamaguchi, K., Milner, C. M., Shineha, R., Satomi, S., and Miyagi, T. (2001). Overexpression of lysosomal-type sialidase leads to suppression of metastasis associated with reversion of malignant phenotype in murine B16 melanoma cells. Int J Cancer 92, 797-804.

Khan, A., Krishna, M., Baker, S. P., and Banner, B. F. (1998a). Cathepsin B and tumor-associated laminin expression in the progression of colorectal adenoma to carcinoma. Mod Pathol 11, 704-708.

Khan, A., Krishna, M., Baker, S. P., Malhotra, R., and Banner, B. F. (1998b). Cathepsin B expression and its correlation with tumor-associated laminin and tumor progression in gastric cancer. Arch Pathol Lab Med 122, 172-177.

Klohs, W. D., and Steinkampf, R. W. (1988). The effect of lysosomotropic agents and secretory inhibitors on anthracycline retention and activity in multiple drug-resistant cells. Mol Pharmacol 34, 180-185.

Leibovitz, A., Stinson, J. C., McCombs, W. B., 3rd, McCoy, C. E., Mazur, K. C., and Mabry, N. D. (1976). Classification of human colorectal adenocarcinoma cell lines. Cancer Res 36, 4562-4569.

Lillehoj, E. P., Hyun, S. W., Feng, C., Zhang, L., Liu, A., Guang, W., Nguyen, C., Luzina, I. G., Atamas, S. P., Passaniti, A., et al. (2012). NEU1 Sialidase Expressed in Human Airway Epithelia Regulates Epidermal Growth Factor Receptor (EGFR) and MUC1 Protein Signaling. J Biol Chem 287, 8214-8231.

Marcos, N. T., Bennett, E. P., Gomes, J., Magalhaes, A., Gomes, C., David, L., Dar, I., Jeanneau, C., DeFrees, S., Krustrup, D., et al. (2011). ST6GalNAc-I controls expression of sialyl-Tn antigen in gastrointestinal tissues. Front Biosci (Elite Ed) 3, 1443-1455.

Marshall, A. D., Lagutina, I., and Grosveld, G. C. (2011). PAX3-FOXO1 induces cannabinoid receptor 1 to enhance cell invasion and metastasis. Cancer Res 71, 7471-7480.

Matarrese, P., Ascione, B., Ciarlo, L., Vona, R., Leonetti, C., Scarsella, M., Mileo, A. M., Catricala, C., Paggi, M. G., and Malorni, W. (2010). Cathepsin B inhibition interferes with metastatic potential of human melanoma: an in vitro and in vivo study. Mol Cancer 9, 207.

Miyagi, T., Sato, K., Hata, K., and Taniguchi, S. (1994). Metastatic potential of transformed rat 3Y1 cell lines is inversely correlated with lysosomal-type sialidase activity. FEBS Lett 349, 255-259.

Monti, E., Bonten, E., D'Azzo, A., Bresciani, R., Venerando, B., Borsani, G., Schauer, R., and Tettamanti, G. (2010). Sialidases in vertebrates: a family of enzymes tailored for several cell functions. In Adv Carbohydr Chem Biochem, D. Horton, ed. (Elsevier Inc.), pp. 403-479.

Ognjanovic, S., Linabery, A. M., Charbonneau, B., and Ross, J. A. (2009). Trends in childhood rhabdomyosarcoma incidence and survival in the United States, 1975-2005. Cancer 115, 4218-4226.

Palmer, R. E., Lee, S. B., Wong, J. C., Reynolds, P. A., Zhang, H., Truong, V., Oliner, J. D., Gerald, W. L., and Haber, D. A. (2002). Induction of BAIAP3 by the EWS-WT1 chimeric fusion implicates regulated exocytosis in tumorigenesis. Cancer Cell 2, 497-505.

Petak, I., Douglas, L., Tillman, D. M., Vernes, R., and Houghton, J. A. (2000). Pediatric rhabdomyosarcoma cell lines are resistant to Fas-induced apoptosis and highly sensitive to TRAIL-induced apoptosis. Clin Cancer Res 6, 4119-4127.

Reddy, A., Caler, E. V., and Andrews, N. W. (2001). Plasma membrane repair is mediated by Ca(2+)-regulated exocytosis of lysosomes. Cell 106, 157-169.

Sabeh, F., Li, X. Y., Saunders, T. L., Rowe, R. G., and Weiss, S. J. (2009). Secreted versus membrane-anchored collagenases: relative roles in fibroblast-dependent collagenolysis and invasion. J Biol Chem 284, 23001-23011.

Safaei, R., Larson, B. J., Cheng, T. C., Gibson, M. A., Otani, S., Naerdemann, W., and Howell, S. B. (2005). Abnormal lysosomal trafficking and enhanced exosomal export of cisplatin in drug-resistant human ovarian carcinoma cells. Mol Cancer Ther 4, 1595-1604.

Sawada, M., Moriya, S., Saito, S., Shineha, R., Satomi, S., Yamori, T., Tsuruo, T., Kannagi, R., and Miyagi, T. (2002). Reduced sialidase expression in highly metastatic variants of mouse colon adenocarcinoma 26 and retardation of their metastatic ability by sialidase overexpression. Int J Cancer 97, 180-185.

Thomas, G. H. (2001). Disorders of glycoprotein degradation and structure: a-mannosidosis, b-mannosidosis, fucosidosis, and sialidosis. In The Metabolic and Molecular Bases of Inherited Disease, C. R. Scriver, A. L. Beaudet, W. S. Sly, and D. Valle, eds. (New York, McGraw Hill, Inc.), pp. 3507-3534.

Uemura, T., Shiozaki, K., Yamaguchi, K., Miyazaki, S., Satomi, S., Kato, K., Sakuraba, H., and Miyagi, T. (2009). Contribution of sialidase NEU1 to suppression of metastasis of human colon cancer cells through desialylation of integrin beta4. Oncogene 28, 1218-1229.

Varki, A., Kannagi, R., Toole, B. P. (2009). Glyosylation Changes in Cancer. In Essentials of Glycobiology, A. Varki, Cummings, R. D., Esko, J. D., Freeze, H. H., Stanley, P., Bertozzi, C. R., Hart, G. W., Etzler, M. E., ed. (Cold Spring Harbor, N.Y., Cold Spring Harbor Laboratory Press).

Walker, T., Marshall, C., Parke, M. A., Yacoub, A., Rahmani, M., Haussinger, D., Reinehr, R., Voelkel-Johnson, C., Fisher, P. B., Grant, S., Dent, P. (2010). 17-Allylamino-17-Demethoxygeldanamycin and MEK 1/2 Inhibitors Kill GI Tumor Cells via $Ca^{2+}$-Dependent Suppression of GRP78/BiP and Induction of Ceramide and Reactive Oxygen Species. Mol Cancer Ther 9, 1378-1395.

Wang, P. H. (2005). Altered Glycosylation in Cancer: Sialic Acids and Sialyltransferases. Journal of Cancer Molecules 1, 73-81.

Warren, L., Jardillier, J. C., and Ordentlich, P. (1991). Secretion of lysosomal enzymes by drug-sensitive and multiple drug-resistant cells. Cancer Res 51, 1996-2001.

Yagi, Y., Machida, A., Tom, S., Kobayashi, T., and Uchihara, T. (2011). Sialidosis type I with neoplasms in siblings: the first clinical cases. Neurol Sci 32, 737-738.

Yogalingam, G., Bonten, E. J., van de Vlekkert, D., Hu, H., Moshiach, S., Connell, S. A., and d'Azzo, A. (2008). Neuraminidase 1 is a negative regulator of lysosomal exocytosis. Dev Cell 15, 74-86.

Yonezawa, S., Goto, M., Yamada, N., Higashi, M., and Nomoto, M. (2008). Expression profiles of MUC1, MUC2, and MUC4 mucins in human neoplasms and their relationship with biological behavior. Proteomics 8, 3329-3341.

Zanoteli, E., de Vlekkert, D. V., Bonten, E. J., Hu, H., Mann, L., Gomero, E. M., Harris, A. J., Ghersi, G., and d'Azzo, A. (2010). Muscle degeneration in neuraminidase 1 deficient mice results from infiltration of the muscle fibers by expanded connective tissue. Biochim Biophys Acta 1802, 659-672.

Example 5: Lysosomal Dysfunction and Excessive Lysosomal Exocytosis Lead to Alzheimer's-Like Amyloidogenesis Abstract:

Lysosomal exocytosis is a regulated physiological process responsible for the controlled secretion of metabolites from specialized secretory cells and for the maintenance of plasma membrane homeostasis in most cell types. The lysosomal sialidase NEU1 is a pivotal negative regulator of this process; genetic ablation of Neu1 in the mouse model of the childhood disease sialidosis leads to exacerbated release of lysosomal content extracellularly with deleterious effects for tissue and extracellular matrix integrity. Here we show that $Neu1^{-/-}$ mice develop pathological and molecular changes in the brain that are reminiscent of Alzheimer's disease (AD). The synergistic action of excessive lysosomal exocytosis of neuronal cells and lysosomal accumulation of oversialylated Neu1 substrates, including the amyloid precursor protein, contribute to the amyloidogenic cascade. In addition, Neu1 downregulation, in a known model of AD, accelerates the amyloidogenic process; conversely, up-regulation of Neu1 in the same model reduces amyloid deposition and plaques formation. These data may explain some of the pathological mechanisms of AD and offer new therapeutic targets along a previously unknown pathway.

Introduction:

Lysosomes are the major site of compartmentalized degradation of glycoproteins, glycolipids, as well as aged organelles, and in this capacity they are pivotal for the maintenance of cell homeostasis. Downregulation or deficiency of any of the lysosomal constituents, whose coordinated activities control overall lysosomal function, disrupts the balance between synthesis and degradation with detrimental effects on multiple tissues and organs. This is particularly true for brain, which is exquisitely sensitive to metabolic changes. One of these fundamental lysosomal enzymes is the sialidase NEU1, which initiates the catabolism of a plethora of sialoglycoconjugate substrates by removing their terminal sialic acids. Aside from its canonical degradative function, NEU1 was recently identified as the enzyme that regulates the physiological process of lysosomal exocytosis (LEX), a function that NEU1 exerts by controlling the sialic acid content of one of its target substrates, the lysosomal associated membrane protein, LAMP1. LEX is a $Ca^{2+}$-dependent regulated mechanism present in virtually all cell types. It begins with the recruitment of a subset of lysosomes along the cytoskeleton to the plasma membrane (PM), followed by their docking at the PM, and fusion with the PM, which releases the lysosomal luminal content into the extracellular space. The docking step of the pathway is mediated by LAMP1. In absence of NEU1, a long-lived, oversialylated LAMP1 specifies an increased number of lysosomes poised to dock at the PM and engage in LEX upon $Ca^{2+}$ influx. The end result is the exacerbated release of lysosomal content extracellularly, which results in abnormal remodeling of the extracellular matrix (ECM) and changes in PM and ECM composition. We determined that many of the systemic abnormalities downstream of NEU1 deficiency in the mouse model of sialidosis could be attributed to excessive LEX, although the downstream effects of this phenotype might vary depending on the physiological characteristics of the affected tissue.

Here we wished to investigate whether deregulated LEX could contribute to the progressive, neuropathological manifestations of the $Neu1^{-/-}$ mice, which reflect those in children with sialidosis.

Results:

We first examined the pattern of expression of Neu1 in the normal brain and demonstrated that the enzyme was widely distributed throughout the parenchyma, with the highest expression in the hippocampus (data not shown). In line with this expression pattern, Lamp1 accumulated in an oversialylated state (data not shown), a feature that correlated with excessive LEX in other cells and tissues of the KO mice. Lamp1 was particularly abundant in activated microglia and in the pyramidal neurons of the $Neu1^{-/-}$ hippocampus (data not shown), suggesting that these cells could exhibit excessive LEX. We tested this possibility by measuring the levels of active lysosomal enzymes in the medium of primary microglia and neurosphere cultures, isolated from $Neu1^{-/-/ARF}$ and $WT^{/ARF}$ mice to increase the number of pluripotent cells and enhance cell viability. Neurospheres from both genotypes had similar cell composition, but the activity of lysosomal β-hexosaminidase (β-hex) was significantly increased only in the media of the Neu1$^{-/-}$ microglia and Neu1$^{-/-/ARF}$ neurospheres (data not shown), confirming the occurrence in these cells of excessive LEX. Notably, the levels of LEX were similar in WT and Neu1$^{-/-}$ primary astrocytes (data not shown), hence we attributed the enhanced exocytic activity measured in the Neu1 deficient neurospheres to the neuronal population of these cultures.

We argued that the increased levels of LEX in Neu1$^{-/-}$ neurons and microglia could dramatically affect the architecture and composition of the brain parenchyma. In fact, histopathological examination of the Neu1$^{-/-}$ brain identified numerous, abnormal eosinophilic bodies, particularly abundant in the CA3 subregion of the hippocampus (data not shown). They were heterogeneous in size and shape, and mostly contained amorphous, granular proteinaceous material, closely resembling the amyloid. These bodies were positive for the histological markers thioflavin S and modified Bielschowsky silver stain (data not shown). Moreover, clusters of these deposits were detected specifically in the CA3 of the Neu1$^{-/-}$ hippocampus by systemic injection of Methoxy-X04, a finding that confirmed the occurrence of an amyloidogenic process downstream of Neu1 deficiency (data not shown). At the ultrastructural level, the amyloid deposits were identified as swollen dystrophic neurites containing numerous vesicles of abnormal morphology and content (data not shown). Combined these phenotypic alterations were reminiscent of those characteristic of Alzheimer's disease (AD). AD is considered a disease of protein aggregates whose composition consists primarily of amyloid precursor protein (APP) abnormally processed into amyloid β-peptides (Aβ) and other proteolytic fragments.

To characterize the amyloid in the brain of Neu1$^{-/-}$ mice, we used antibodies cross-reacting with full length APP and found a progressive and time dependent accumulation of this protein in the pyramidal neurons of the CA3 region (data not shown). Ubiquitin and neurofilaments antibodies also immunostained most of the APP+ dystrophic neurites, suggesting extensive cytoskeletal abnormalities in these structures (data not shown). Accumulation of APP was confirmed by immunoblots of hippocampal lysates that demonstrated a marked increase of this protein in Neu1$^{-/-}$ samples (data not shown). Because it is well established that increased expression of APP in both AD and Down syndrome patients represents a risk factor for the development of the disease, we inferred that NEU1 loss of function could predispose to an AD-like phenotype.

APP is a type-I membrane glycoprotein, which is glycosylated and sialylated; changes in its glycan makeup have been linked to aberrant processing of the protein leading to increased production and secretion of toxic Aβ peptides. We hypothesized that APP could be a natural substrate of Neu1 and, if so, would accumulate in an oversialylated state in absence of Neu1 activity. Indeed, analysis of APP in Neu1$^{-/-}$ hippocampal lysates with sambucus nigra lectin (SNA) confirmed the presence of excess amounts of α-2,6 linked sialic acids on the protein (data not shown). In vitro enzymatic removal of all N- and O-glycans released a core-APP protein that was identical in size in the Neu1$^{-/-}$ and WT samples, indicating that APP conformational changes in the Neu1$^{-/-}$ brain were due to impaired removal of its sialic acids (data not shown). Accumulated APP was also detected in crude lysosomal fractions (CLF) isolated from the KO hippocampi, together with two other substrates of Neu1 (data not shown), Lamp1 and cathepsin B. These results identify APP as a novel substrate of Neu1 that could be at least in part cleaved in the lysosomal compartment.

A crucial step in the amyloidogenic processing of APP is the generation of carboxy terminal fragments (CTFs), which are subsequently cleaved into β-amyloid. We therefore assessed their levels in Neu1$^{-/-}$ samples, as predictive measure of abnormal Aβ processing. CTFs levels were increased in both Neu1$^{-/-}$ hippocampal samples and in CLF compared to those in WT samples (data not shown). Furthermore, β-amyloid was abnormally present in Neu1$^{-/-}$ CLF (data not shown) suggesting that oversialylated APP is processed in the lysosomal compartment. These observations were further supported by the detection of elevated amounts of the amyloid peptide Aβ42 (Aβ) both in the culture media of Neu1$^{-/-/ARF}$ neurospheres, and in the KO cerebrospinal fluid (data not shown). To ascertain the role of LEX in this amyloidogenic process, we cultured Neu1$^{-/-/ARF}$ and Neu1$^{WT/ARF}$ neurospheres in presence of a human TAMRA-conjugated, fluorescent Aβ42 (T-Aβ). T-Aβ was readily taken up by the cells and rerouted to late endosomes/lysosomes (data not shown). This fraction of the internalized peptide was then trafficked from the lysosomes to the PM via LEX, as determined by live imaging of lysotracker-labeled lysosomes with total internal reflection microscopy (data not shown). By counting the number of lysotracker+ organelles proximal to the PM we showed that Neu1$^{-/-/ARF}$ cells had significantly higher number of T-Aβ-containing lysosomes clustered at the PM (data not shown). Moreover, when both neurosphere cultures were maintained in T-Aβ free medium for 24 h following exposure to the peptide we were able to capture the T-Aβ fluorescence released extracellularly, and consequently we measured increased amounts of T-Aβ exocytosed into the medium of Neu1$^{-/-/ARF}$ cells compared to WT cells (data not shown). Thus, Aβ is abnormally secreted in absence of Neu1 and is released via LEX.

Together these results suggest that Neu1 loss of function and consequent exacerbation of LEX are predisposing factors to β-amyloidogenesis. To further verify this assumption, we analyzed the effects of Neu1 ablation on amyloid β levels and plaque formation in vivo by using a well characterized transgenic model of AD (5XFAD) that we crossed into the Neu1$^{-/-}$ background. We first tested the expression levels of Neu1 in the 5XFAD mouse line by immunohistochemistry. We observed a marked downregulation of the enzyme, especially noticeable in the hippocampus, which was accompanied by increased expression of Lamp1 (data not shown). We also measured reduced Neu1 enzyme activity in primary neurospheres isolated from the 5XFAD hippocampi (data not shown). To further these observations, we demonstrated that the levels of APP were increased in hippocampal lysates isolated from 5XFAD/Neu1$^{-/-}$ compared to those in 5XFAD/WT (data not shown). Moreover, APP processing in these mice resulted in the accumulation of amyloid-β (data not shown), a finding that supports the idea that downregulation or loss of Neu1 in 5XFAD mice accelerates the β-amyloidogenic process likely via deregulated LEX.

Finally, to test whether Neu1 deficiency (and excessive LEX) could represent a therapeutic target to revert an AD-like phenotype, we sought to exogenously increase Neu1 activity in the brain of 5XFAD mice. The latter could be achieved by augmenting the intracellular expression of the Neu1 chaperone Protective Protein Cathepsin A (PPCA). We therefore performed stereotactic injection of an adeno-associated virus containing both human NEU1 and PPCA (AAVNEU1/AAVPPCA) into the hippocampal region of the 5XFAD mice. This vector combination directed sustained expression of the transgenes in vitro (data not shown). Four weeks after injection, high expression of both PPCA and NEU1 was detected in brain sections of mice treated with the recombinant AAV vectors (data not shown). Remarkably, the abundant number of amyloid plaques seen in the untreated 5XFAD mice was reduced by 44.3±6.2% in the AAV injected mice, compared to the same line injected only with carrier solution (data not shown). Immunoblots of hippocampal lysates from the injected 5XFAD mice confirmed that both APP and β-amyloid levels were reduced (data not shown).

CONCLUSIONS

In conclusion our results reveal an unsuspected mechanism of control over APP processing by a lysosomal enzyme. We propose a two-hit model to explain the amyloidogenic process downstream of Neu1 loss of function: the accumulation of an oversialylated APP which is abnormally processed, followed by the release of APP end products via excessive LEX. In this scenario the activated microglia with increased LEX could engage in a feed forward pathogenic cascade by releasing active lysosomal enzymes extracellularly that may cleave APP, producing toxic Aβ peptides. Neu1 position in the amyloidogenic pathway and its role as central regulator of LEX may be exploited for new potential therapeutic targets to treat/delay plaque deposition and amyloid formation in AD.

That which is claimed:

1. A method of treating dementia associated with Alzheimer's disease in a human subject comprising administering to the human subject a therapeutically effective amount of a composition comprising a recombinant viral vector encoding a Protective Protein/Cathepsin A (PPCA) polypeptide.

2. The method of claim 1, wherein the PPCA polypeptide comprises SEQ ID NO: 4.

3. The method of claim 2, wherein the recombinant viral vector comprises a nucleotide sequence having at least 85% identity to SEQ ID NO: 3.

4. The method of claim 1, wherein the recombinant viral vector is an adenovirus-associated viral (AAV) vector.

5. The method of claim 1, further comprising administration of a composition comprising a recombinant viral vector encoding a Neuraminidase 1 (NEU1) polypeptide.

6. The method of claim 5, wherein the NEU1 polypeptide comprises SEQ ID NO: 2.

7. The method of claim 6, wherein the NEU1 polypeptide is encoded by a nucleotide sequence having at least 85% identity to SEQ ID NO: 1.

8. The method of claim 5, wherein the recombinant viral vector encoding a NEU1 polypeptide is an AAV vector.

9. The method of claim 5, wherein the composition comprising a recombinant viral vector encoding a PPCA polypeptide and the composition comprising a recombinant viral vector encoding a Neuraminidase 1 (NEU1) polypeptide are administered simultaneously.

10. The method of claim 5, wherein the composition comprising a recombinant viral vector encoding a PPCA polypeptide and the composition comprising a recombinant viral vector encoding a Neuraminidase 1 (NEU1) polypeptide are administered separately.

11. The method of claim 1, further comprising the administration of one or more additional drugs for treating dementia associated with Alzheimer's disease.

12. The method of claim 11, wherein the one or more additional drugs is selected from donepezil, galantamine, memantine, rivastigmine and tacrine.

13. The method of claim 1, wherein the composition is administered parenterally.

14. The method of claim 13, wherein the composition is administered intravenously.

15. The method of claim 13, wherein the composition is administered via intra-arteriole, intramuscular, intradermal, subcutaneous, intraperitoneal, intraventricular, or intracranial administration.

16. The method of claim 1, wherein the composition is administered with a pharmaceutically acceptable carrier.

* * * * *